US008426179B2

(12) United States Patent
Messersmith et al.

(10) Patent No.: US 8,426,179 B2
(45) Date of Patent: Apr. 23, 2013

(54) SYNTHETIC PEPTIDE AND PEPTIDE CONJUGATES AND RELATED TISSUE COUPLING METHODS VIA TRANSGLUTAMINASE ENZYME

(75) Inventors: Phillip B. Messersmith, Clarendon Hills, IL (US); Marsha Ritter-Jones, Chicago, IL (US)

(73) Assignee: Northwestern University, Evanston, IL (US)

( * ) Notice: Subject to any disclaimer, the term of this patent is extended or adjusted under 35 U.S.C. 154(b) by 1081 days.

(21) Appl. No.: 12/231,361

(22) Filed: Sep. 2, 2008

(65) Prior Publication Data

US 2009/0061014 A1 Mar. 5, 2009

Related U.S. Application Data

(60) Provisional application No. 60/969,081, filed on Aug. 30, 2007.

(51) Int. Cl.
*C12N 9/10* (2006.01)
*A61K 38/00* (2006.01)
*A61K 38/04* (2006.01)

(52) U.S. Cl.
USPC ............ 435/193; 530/300; 530/329; 530/331

(58) Field of Classification Search .................. None
See application file for complete search history.

(56) References Cited

U.S. PATENT DOCUMENTS

| 6,267,957 B1 * | 7/2001 | Green et al. ................. 424/94.5 |
| 6,919,076 B1 | 7/2005 | Green et al. |
| 7,208,171 B2 * | 4/2007 | Messersmith et al. ........ 424/422 |

OTHER PUBLICATIONS

Hu, B-H; Ritter Jones, M; Messersmith, PB. Method for Screening and MALDI-TOF MS Sequencing of Encoded Combinatorial Libraries. Anal. Chem. 2007, 79, pp. 7275-7285. Published on Web Aug. 23, 2007.
Ritter Jones, M; Messersmith, P. Facile coupling of synthetic peptides and peptide-polymer conjugates to cartilage via transglutaminase enzyme. Biomaterials. Dec. 2007; 28(35):5215-5224.
Chau, DYS; Collighan, RJ; Verderio, EAM; Addy, VL; Griffin, M. The cellular response to transglutaminase-cross-linked collagen. Biomaterials 26 (2005) pp. 6518-6529.
Fesus, L; Metsis, ML; Muszbek, L; Koteliansky, VE. Transglutaminase-sensitive glutamine residues of human plasma fibronectin revealed by studying its proteolytic fragments. Eur. J. Biochem. 154, pp. 371-374 (1986).
Skorstengaard, K; Halkier, T; Højrup, P; Mosher, D. Sequence location of a putative transglutaminase cross-linking site in human vitronectin. FEBS, vol. 262, No. 2, pp. 269-274, Mar. 1990.
Raghunath, M; Cankay, R; Kubitscheck, U; Fauteck, JD; Mayne R; Aeschlimann, D; Schlötzer-Schrehardt, U. Transglutaminase Activity in the Eye: Cross-linking in Epithelia and Connective Tissue Structures. Investigative Ophthalmology & Visual Science, Nov. 1999, vol. 40, No. 12, pp. 2780-2787.
Sane, DC; Moser, TL; Parker, CJ; Seiffert, D; Loskutoff, DJ; Greenberg, CS. Highly Sulfated Glycosaminoglycans Augment the Cross-linking of Vitronectin by Guinea Pig Liver Transglutaminase. The Journal of Biological Chemistry, vol. 256, No. 6, pp. 3543-3548, 1990.
Aeschlimann, D; Paulsson, J; Mann, K. Identification of Gln726 in Nidogen as the Amine Acceptor in Transglutaminase-catalyzed Cross-linking of Laminin-Nidogen Complexes. The Journal of Biological Chemistry, vol. 267, No. 16, Issue of Jun. 5, pp. 11316-11312, 1992.
Hohenadl, C; Mann, K; Mayer U; Timpl, R; Paulsson, M; Aeschlimann, D. Two adjacent N-terminal Glutamines of BM-40 (Osteonectin, SPARC) Act as Amine Acceptor Sites in TraneglutaminaseC-catalyzed Modification, The Journal of Biological Chemistry, vol. 270, No. 40, Issue of Oct. 6, pp. 23415-23420, 1995.
Orban, JM; Wilson, LB; Kofroth, JA; El-Kurdi, MS; Maul, TM; Vorp, DA. Crosslinking of collagen gels by transglutaminase. J. Biomed, Mat, Res. 68A: pp. 756-762, 2004.
Aeschlimann, D; Wetterwald, A; Fleisch, H; Paulsson, M. Expression of Tissue Transglutaminase in Skeletal Tissues Correlates with Events of Terminal Differentiation of Chondrocytes. The Journal of Cell Biology, vol. 120, No. 6, Mar. 1993, pp. 1461-1470.
Aeschlimann, D; Kaupp, O; Paulsson, M. Transglutaminase-catalyzed Matrix Cross-linking in Differentiating Cartilage: Identification of Osteonectin as a Major Glutaminyl Substrate. The Journal of Cell Biology, vol. 129, No. 3, May 1995, pp. 881-892.
Hu, B-H; Messersmith, PB. Rational Design of Transglutaminase Substrate Peptides for Rapid Enzymatic Formation of Hydrogels. J. Am. Chem. Soc., vol. 125, No. 47, 2003, pp. 14298-14299.
Lorand, L; Graham, RM. Transglutaminases: Crosslinking Enzymes with Pleiotropic Functions. Nature, vol. 4. Feb. 2003, pp. 140-156.
Jürgensen, K; Aeschlimann, D; Cavin, V; Genge, M; Hunziker, EB. A New Biological Glue for Cartilage—Cartilage Interfaces: Tissue Transglutaminase. The Journal of Bone and Joint Surgery, Incorporated, Vol, 79-A, No. 2, Feb. 1997, pp. 185-193.
Prince, CW; Dickie, D; Krumdieck, CL. Osteopontin, A Substrate for Transglutaminase and Factor XIII Activity. Biochemical and Biophysical Research Communications, vol. 177, No. 3, pp. 1205-1210, Jun. 28, 1991.
Sørensen, ES; Rasmussen, LK; Møller, L; Jensen, PH; Højrup, P; Petersen, TE. Localization of transglutaminase-reactive glutamine residues in bovine osteopontin. Biochem J. (1994) 304, pp. 13-16.

(Continued)

*Primary Examiner* — Tekchand Saidha
*Assistant Examiner* — Md. Younus Meah
(74) *Attorney, Agent, or Firm* — Reinhart Boerner Van Deuren S.C.

(57) ABSTRACT

Peptides and conjugates thereof comprising one or more bioactive agents which can be coupled to a tissue via a transglutaminase and related methods.

20 Claims, 17 Drawing Sheets

OTHER PUBLICATIONS

Kleman, J-P; Aeschlimann, D; Paulsson, M; Van Der Rest, M. Transglutaminase-Catalyzed Cross-Linking of Fibrils of Collagen V/XI in A204 Rhabdomyosarcoma Cells. Biochemistry, 1995, vol. 34, No. 42, pp. 13768-13775.

Sanborn, TJ; Messersmith, PB; Barron, AE. In situ crosslinking of a biomimetic peptide-PEG hydrogel via thermally triggered activation of factor XIII, Biomaterials 23 (2002), pp. 2703-2710.

Hu, B-H; Messersmith, PB. Enzymatically cross-linked hydrogels and their adhesive strength to biosurfaces. Orthodontics & Craniofacial Research (2005), 8(3), 145-9. *Abstract*.

Jones, et al. Enzymatic Cross-linking of Short Synthetic Peptides and Peptide-polymer Conjugates to Cartilage. Symposium N. Polymer Gels for Emerging Technologies, 2005 p. 353, col. 2:p. 354 col. 1.

* cited by examiner

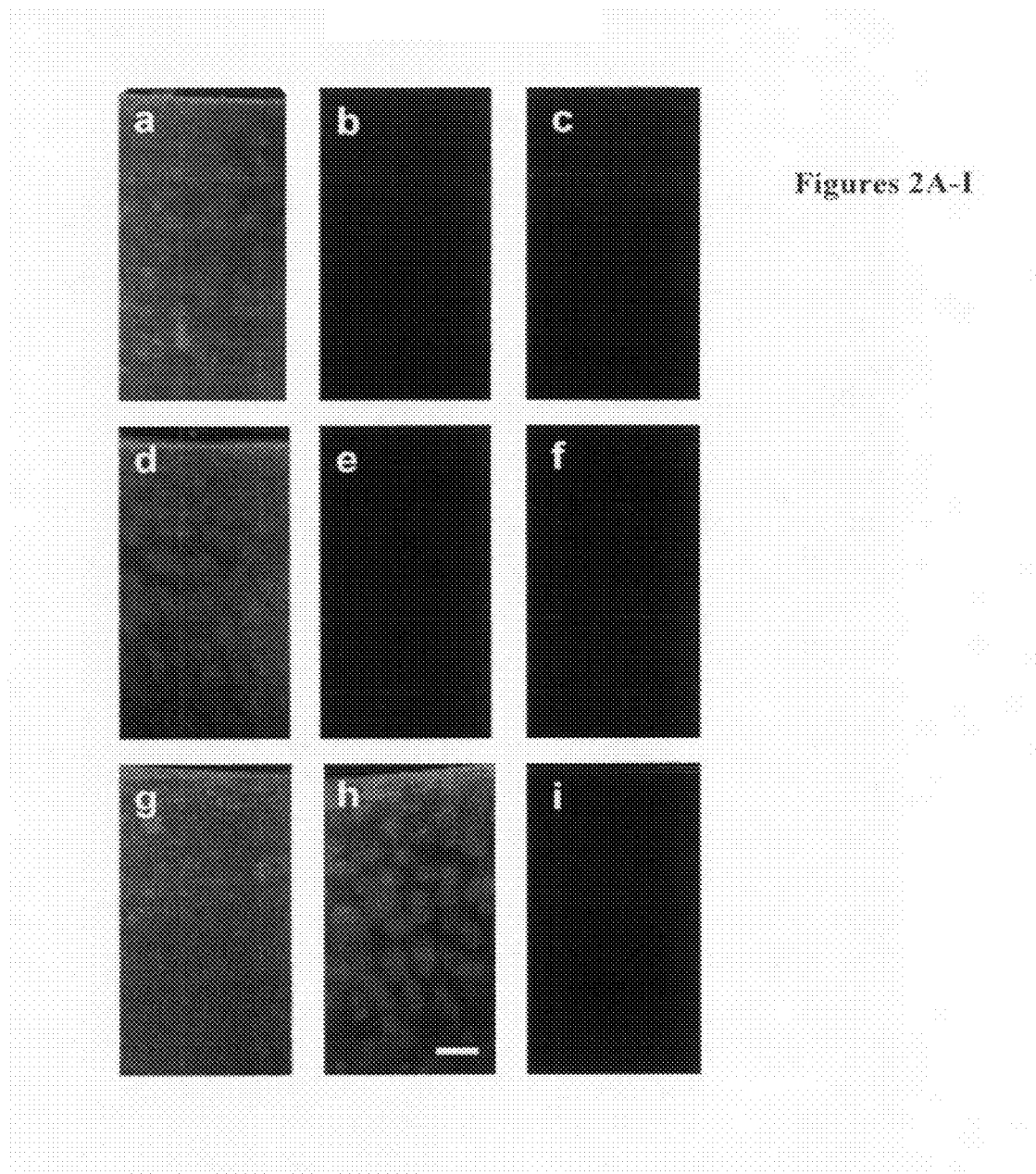
Figures 2A-I

Figure 5A
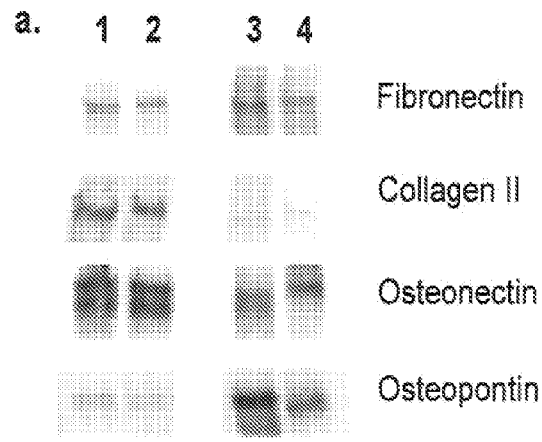
Figure 5B-E
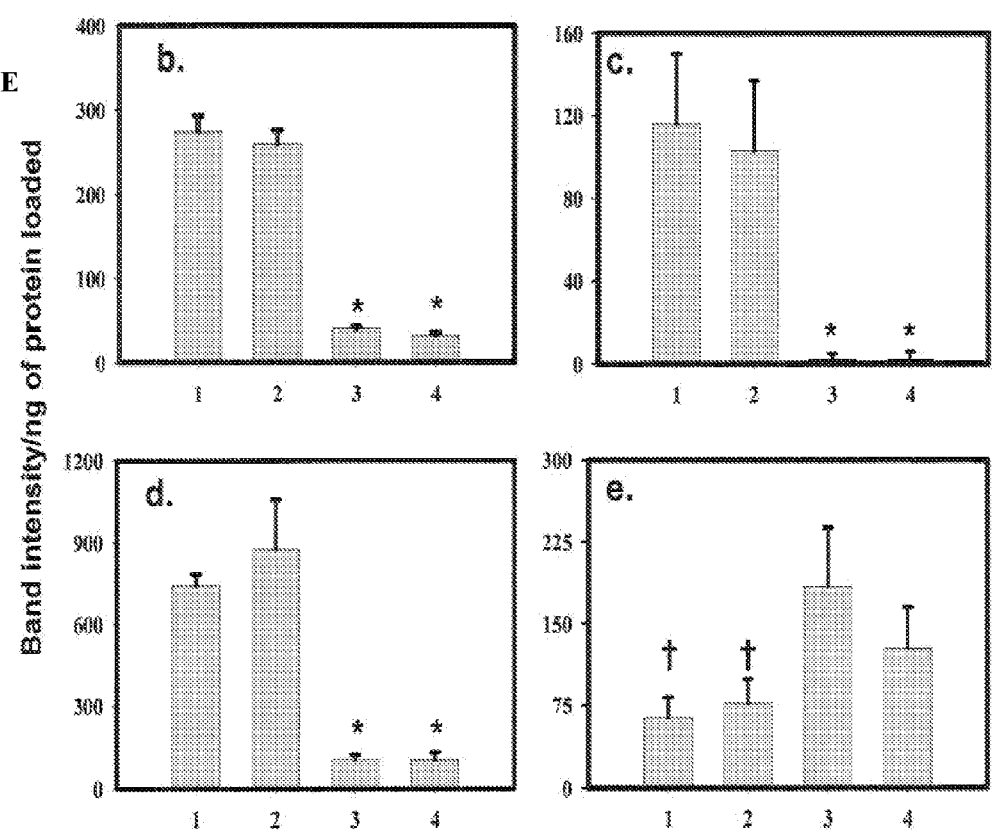

Figure 11A
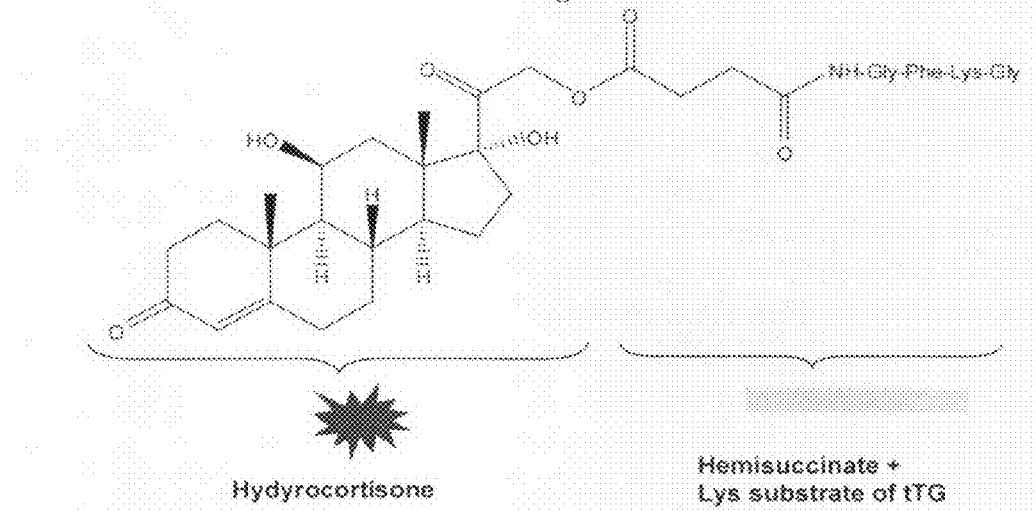
Hydrocortisone | Hemisuccinate + Lys substrate of tTG
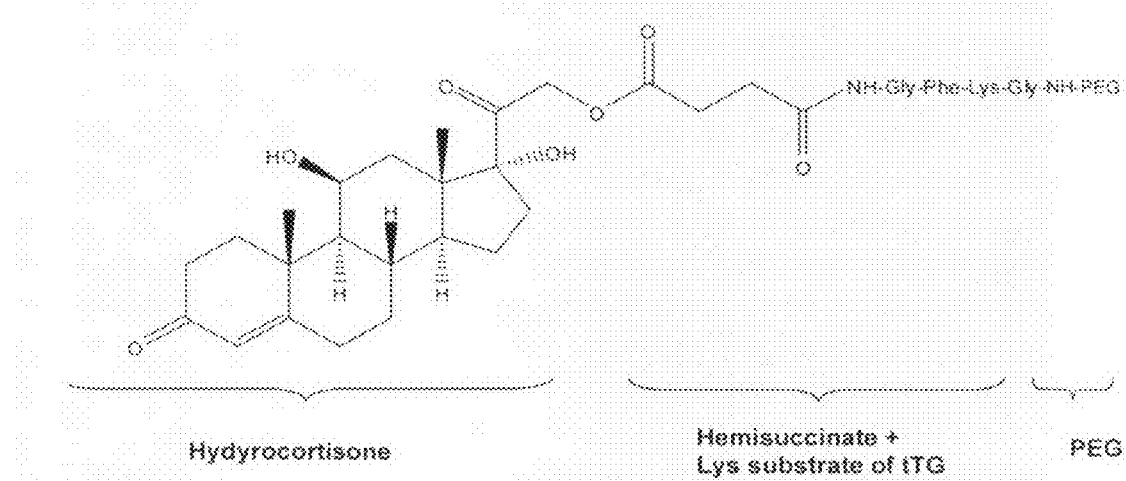
Hydrocortisone | Hemisuccinate + Lys substrate of tTG | PEG
Figure 11B

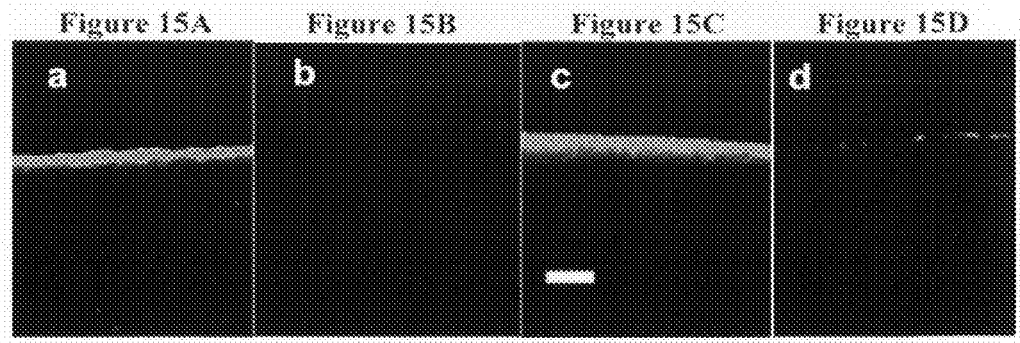
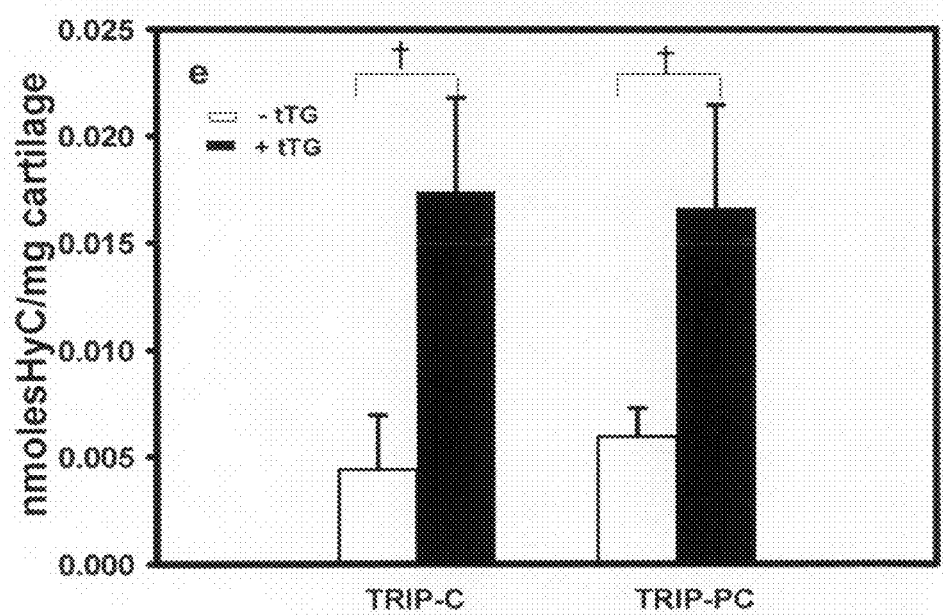
Figure 15E

SYNTHETIC PEPTIDE AND PEPTIDE CONJUGATES AND RELATED TISSUE COUPLING METHODS VIA TRANSGLUTAMINASE ENZYME

This application claims priority benefit from application Ser. No. 60/969,081, filed Aug. 30, 2007, the entirety of which is incorporated herein by reference.

This invention was made with government support under DE013030 awarded by the National Institutes of Health. The government has certain rights in the invention.

BACKGROUND OF THE INVENTION

Strategies for chemically coupling natural or synthetic molecules to biological surfaces are important tools for drug delivery, tissue repair, and fixation of tissue engineered scaffolds for tissue regeneration. Several methods are capable of attenuating, inhibiting or promoting interactions between tissue surfaces as well as between the cells and extracellular matrix (ECM) proteins that comprise them. Electrostatic interactions have been employed by Elbert et al. in the form of poly-L-lysine-graft-(poly(ethylene glycol) polymers that chemisorb to proteins on tissue surfaces, and this approach was explored as a strategy to minimize postsurgical adhesions. Winblade et al. employed phenylboronic acid modified polymers to provide reversible covalent crosslinks to cis-diols in sugar residues of glycoproteins and polysaccharides. Layer by layer (LbL) assembly of polyelectrolytes has been used to apply polymer coatings onto model biological surfaces, the surface of blood vessels and pancreatic islets.

Specific functional groups found in ECM proteins have been exploited for covalent surface modification strategies. For example, 1-ethyl-3-(3-dimethylaminopropyl)carbodiimide (EDC) and N-hydroxysuccinimide (NHS) have been used extensively to couple macromolecules containing carboxylic acids to protein amines. Amine-reactive PEG diisocyanates have been used to modify pancreatic islets in order to provide immunoprotection, to create a barrier to platelet adhesion on damaged arteries, and on preclotted Dacron and other model biological surfaces. Aldehyde modified chondroitin sulfate, which also reacts with tissue amines, has been used as a tissue adhesive in both the cornea and cartilage. Photochemical oxidation of native tyrosine residues in collagen II has been used to improve the integration of photopolymerized hydrogels with cartilage.

In contrast to chemical or photochemical approaches, a general strategy for tissue surface modification is directed to biological enzyme mediated crosslinking reactions. Transglutaminases (TG) are calcium-dependent enzymes that catalyze crosslinking between lysine and glutamine residues to form ε-(γ-glutaminyl)lysine isopeptide bonds. (See, Lorand L and Graham R M. Transglutaminases: Crosslinking enzymes with pleiotropic functions. Nature Reviews Molecular Cell Biology 2003; 4: 140-156.) There is growing interest in the use of transglutaminase enzymes for tissue repair and reconstruction. Calcium-independent microbial TG has been used to develop gelatin hydrogels for biomedical adhesives as well as for in vitro expansion of cells. Factor XIII, the circulatory form of TG, has been used to form fibrin matrices for in vitro and in vivo studies of neurite growth, angiogenesis, and cartilage regeneration. The incorporation of bioactive peptides and proteins into these matrices was achieved by including a Factor XIII reactive peptide domain within the molecule. Synthetic polymers have also been modified with Factor XIII substrate peptides, which were then crosslinked by the enzyme into a hydrogel. (See, Sanborn T J, Messersmith P B, and Barron A E. In situ crosslinking of a biomimetic peptide-PEG hydrogel via thermally triggered activation of factor XIII. Biomaterials 2002; 23: 2703-2710.)

A transglutaminase enzyme found in many connective tissues and often referred to as tissue transglutaminase (tTG) was used to form hydrogels through crosslinking of glutamine modified poly(ethylene glycol) (PEG) polymers and a lysine containing polyaminoacid. Hu et al. subsequently employed rationally designed peptide substrates of tTG to modify PEG polymers to form an adhesive hydrogel. (See, e.g., Hu B and Messersmith P. Rational design of transglutaminase substrate peptides for rapid enzymatic formation of hydrogels. Journal of the American Chemical Society 2003; 125: 14298-14299; and Hu B and Messersmith P. Enzymatically cross-linked hydrogels and their adhesive strength to biosurfaces. Orthodontic and Craniofacial Research 2005; 8: 145-149.) More recently, tTG has also been used to couple biomolecules to insoluble peptide assemblies, and was used to enhance cell adhesion and spreading on collagen matrices and synthetic polymers coated with fibronectin.

Relating more specifically to a particular disease state, over 70 million people in the US are afflicted with the debilitating pain and inflammation of osteoarthritis (OA), caused primarily by the action of the potent catabolic cytokine interleukin 1 (IL-1). The effects of IL-1 include increased production of matrix metalloproteases and other inflammatory cytokines, inhibition of extracellular matrix (ECM) synthesis, and cell death. Glucocorticoids down regulate the transcription and translation of IL-1, and hence are a major treatment strategy for reducing the pain and inflammation of OA. Locally administered via intra-articular injections to maximize their effects at the inflamed joint and to minimize adverse systemic effects, glucocorticoids are insoluble suspensions which precipitate in the joint space. Nevertheless, a significant portion of the drug dose is still cleared from the joint, entering the circulatory system and exerting unwanted systemic effects including a drop in endogenous cortisol levels, temporary disruption in glucose metabolism, and immunosuppression. In addition, precipitated crystals of glucocortiods may potentially induce inflammation.

Several approaches have been proposed to increase the retention of glucocorticoids in the inflamed joint, mostly relying on introduction of drug-laden vehicles into the intra-articular space. Liposomes of glucocorticoid palmitate esters have been shown to be more effective in reducing knee swelling than the free drug alone. Another method to improve glucocorticoid retention in the joint capsule is modification of hyaluronan (HA) with methyl prednisolone, which method was shown to have better antioxidant properties on chondrocytes than when the two compounds were administered individually. Microspheres and nanospheres have also been utilized as local drug delivery vehicles to joints. However, performance can be problematic and dependent on factors such as the molecular weight and type of polymer used to form the spheres, the extent of crosslinking and particle size. However, such strategies to retain glucocorticoids in the joint space also rely on precipitation of the drug vehicle in the joint, which can lead to problems of the sort encountered with current treatments: potential inflammation and/or elimination via the lymphatic system. As such, there remains in the art an on-going search for an alternate approach for delivery and retention—to realize the benefits associated with such therapeutics.

SUMMARY OF THE INVENTION

In light of the foregoing, it is an object of the present invention to provide various bioactive and/or therapeutic compounds, compositions and/or methods for their use and delivery, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide an alternate approach to binding a bioactive agent or prodrug thereof to a specific tissue, as can be accomplished using an endogenous or exogenous tissue enzyme.

It can be another object of the present invention to provide for release of such a bound bioactive agent under physiological conditions.

It can be another object of the present invention to enhance efficiencies in administration and delivery of a bioactive agent to a specific tissue target.

It can be another object of the present invention, alone or in conjunction with one or more of the preceding objectives, to provide a molecular platform or architecture for targeted delivery of various and diverse bioactive agents to a wide range of tissue targets.

Other objects, features, benefits and advantages of the present invention will be apparent from the summary and the following descriptions of certain embodiments, and be readily apparent to those skilled in the art having knowledge of various drug delivery systems and related methodologies. Such objects, features, benefits and advantages will be apparent from the above as taken into conjunction with the accompanying examples, data, figures and all reasonable inferences to be drawn therefrom, alone or with consideration of the references incorporated herein.

In part, this invention can be directed to peptide conjugate compounds. Such a compound can comprise a bioactive agent; a peptide component comprising a lysinyl and/or a glutaminyl substrate of a transglutaminase enzyme, and a component coupling such an agent to such a peptide, such a coupling component cleavable under physiological conditions. As would be understood by those skilled in the art made aware of this invention, such a lysinyl substrate can comprise a lysine residue and/or another residue, component and/or moiety capable of amine donor function in the presence of a transglutaminase. Such a glutaminyl substrate can comprise a glutamine residue and/or another residue, component and/or moiety capable of acyl donor function in the presence of a transglutaminase. Likewise, as would be understood by those skilled in the art made aware of this invention, such substrates are limited only by amine or acyl donor function sufficient for or in the context of transglutaminase activity. In certain non-limiting embodiments, such a peptide component can comprise a sequence comprising FKG and/or GQQQLG (SEQ ID NO: 1). Regardless, such a coupling moiety can be hydrolysable, such a moiety including but not limited to an ester.

With regard to the compounds, compositions and/or methods of this invention, any such lysinyl and/or glutaminyl substrate can be considered in the context of one or more transglutaminase enzymes of the sort discussed herein or as would otherwise be known to those skilled in the art. In certain non-limiting embodiments of this invention, such an enzyme can be selected from tissue transglutaminase enzymes or combinations thereof. In certain other embodiments, such an enzyme can be selected from bacterial transglutaminase enzymes and circulatory transglutaminase (e.g., Factor VIII) enzymes or combinations thereof. Any such enzyme is limited only by function sufficient to couple or cross-link lysinyl and glutaminyl substrates and/or to form ε-(γ-glutaminyl)lysine isopeptide bonds.

Regardless, without limitation as to peptide component or coupling moiety, such a bioactive agent can comprise a prodrug thereof. In certain embodiments, such an agent can be a prodrug of a glucocorticoid. In certain such non-limiting embodiments, such an agent can be a prodrug of hydrocortisone. Without limitation as to the identity of any particular bioactive agent or peptide component, such a compound can be coupled to a tissue substrate comprising one or more ECM components. In certain such embodiments, including those where a bioactive agent comprises a glucocorticoid or a prodrug thereof, such a compound can be coupled to cartilage and/or meniscus tissues.

In part, this invention can also be directed to one or more pharmaceutical compositions. Such a composition can comprise a peptide conjugate compound of the sort discussed above, illustrated elsewhere herein, or would otherwise be understood by one skilled in the art made aware of this invention and/or a pharmaceutically-acceptable salt thereof. Likewise, such compositions can also comprise a pharmaceutically-acceptable carrier. Regardless, in certain such embodiments, such a composition can comprise a transglutaminase to promote compound coupling or binding to a particular tissue substrate.

In part, the present invention can also be directed to a method of tissue modification. Such a method can comprise providing a peptide conjugate compound of this invention; and contacting such a compound and a tissue substrate comprising a lysinyl and/or a glutaminyl substrate, such contact in the presence of a transglutaminase enzyme, such contact and/or enzyme present at least partially sufficient to bind such a compound and tissue substrate. In certain such embodiments, such a substrate can comprise one or more ECM components. Regardless, such a transglutaminase enzyme can be endogenous to such a tissue or introduced in conjunction with such a peptide conjugate. Upon such tissue modification, providing a compound with cleavable and/or hydrolysable coupling component, such an agent can be released from the compound and/or delivered to such a tissue substrate.

Accordingly, the present invention can also be directed to a method of using transglutaminase activity to deliver a therapeutic agent. Such a method can comprise providing a peptide conjugate compound, of the sort described herein, comprising a prodrug component of a therapeutic agent; a peptide component comprising at least one of a lysinyl and a glutaminyl substrate for a transglutaminase, and a component coupling such an agent to such a peptide, such a coupling component hydrolysable under physiological conditions; contacting such a compound and a tissue substrate comprising a lysinyl and/or a glutaminyl substrate, such contact in the presence of a transglutaminase enzyme, such contact and or enzyme presence at least partially sufficient for compound and tissue binding; and hydrolyzing such a compound, to release the therapeutic agent.

Without limitation and as illustrated elsewhere herein, one especially useful embodiment of this invention can be directed to a compound comprising a prodrug of a glucocorticoid, such as but not limited to hydrocortisone. In the presence of a transglutaminase enzyme, whether endogenous or otherwise introduced, such a compound can be coupled to cartilage and/or meniscus tissue. Hydrolysis under physiological conditions can provide for release of a therapeutic agent (e.g., hydrocortisone) for desired therapeutic effect.

As illustrated by several non-limiting embodiments, this invention can be directed to the use of a tTG enzyme as part of a simple and biocompatible approach for coupling one or more therapeutic agents to tissue surfaces. Without limitation, cartilage is a representative tissue for use with this invention, as it is contains tTG as well as several ECM substrates of tTG. In certain embodiments, synthetic peptides comprising, without limitation, lysine and/or glutamine residues and conjugates of such peptides with another molecule, polymer, and/or therapeutic agent can be bound to cartilage surfaces through the action of a tTG enzyme. As discussed below, several cartilage ECM components can be substrates for the reaction. Given the existence of macromolecular tTG substrates in many tissues, this facile approach to tissue modification can be broadly applicable to a variety of tissues for localization of a range of biologically active and/or therapeutic agents and for enhancing (or inhibiting) adhesion at tissue-tissue and tissue-device interfaces.

One non-limiting embodiment, representative of various broader aspects of this invention, can be directed to immobilization of one or more glucocorticoids (and, more broadly, any drug or prodrug) to tissue surfaces for localized therapeutic delivery. Unlike the aforementioned prior art techniques of localized drug delivery, many of which depend on precipitation of the drug delivery vehicle, an approach of this invention covalently attaches the drug to the tissue surface making it resistant to natural fluid turnover in the joint space. In certain embodiments, a peptide substrate, such as but not limited to FKG, can be conjugated to hydrocortisone hemisuccinate, forming a prodrug, TRIP-C (i.e., a transglutaminase immobilized prodrug on cartilage), and can then be coupled to the articular surface of cartilage or to the meniscus. PEGylated or other polymeric variations or forms of such prodrugs (i.e., TRIP-PC) can also be prepared as described herein and used to determine and/or affect tissue binding, prodrug stability and/or delivery.

BRIEF DESCRIPTION OF THE DRAWINGS

FIGS. 2A-I. Representative digital images of fluorescent anti-biotin antibody stained cartilage sections after reaction with peptide-PEG conjugates and tTG. A) B2K; B) B2K without tTG; C) B2O; D) B2Q; E) B2Q without tTG; F) B2N; G) B72K; H) B72Q; I) B72. Scale bar represents 25 μm for all images. The articular surface is located at the top of each image.

FIGS. 5A-E. Reactivity of peptide-PEG conjugates toward cartilage ECM proteins. a) Digital images of Western blot analysis of individual cartilage proteins, showing their reactivity with each peptide-PEG conjugate. Lane 1=B2K, Lane 2=B72K, Lane 3=B2Q, and Lane 4=B72Q. B-E. Comparison of the band intensity normalized by the amount of protein loaded. B) Fibronectin. C) Type II collagen. D) Osteonectin. E) Osteopontin. Bar labels are for each peptide-PEG conjugate as defined in panel a. *, $p<0.05$ as compared to B2K or B72K. †, $p<0.05$ as compared to B2Q. Error bars represent standard deviation.

FIGS. 11A-B. Molecular structures of prodrugs. A) Molecular structure of TRIP-C and pictographic representation of each component. B) Molecular structure of TRIP-PC.

FIGS. 15A-E. Comparison of the amount of TRIP-C and TRIP-PC coupled to the articular surface via tTG. A-D) Immunohistochemistry. Digital images illustrating detection of hydrocortisone with anti-hydrocortisone antibody and a fluorescein conjugated secondary antibody. Coupling reactions were performed in Buffer 3 with 1.0 mM of the prodrug. A) TRIP-C with tTG; B) TRIP-C; C) TRIP-PC with tTG; D) TRIP-PC. Bar represents 30 µm. e) Graph quantifying the amount of hydrocortisone detected at the conditions described above for A-D. Error bars represent standard deviation. †, p<0.05 comparing samples treated with and without tTG.

DETAILED DESCRIPTION OF CERTAIN EMBODIMENTS

Figure 1:
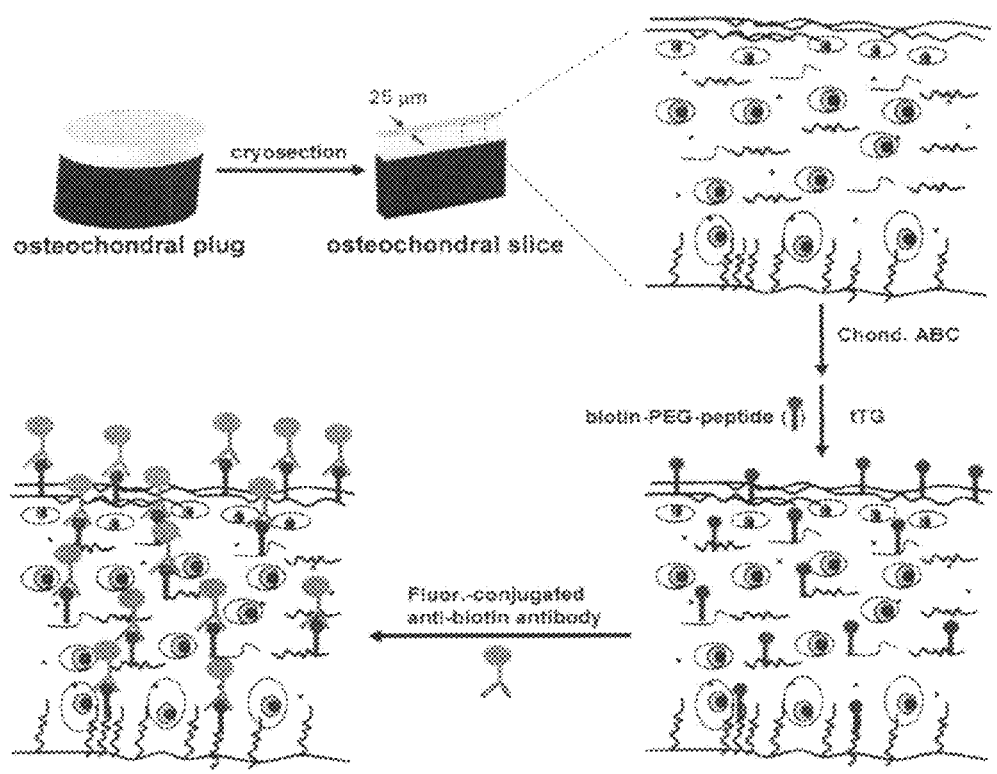
FIG. 1. Schematic overview of the experimental methods used for reaction of synthetic peptides with cartilage tissue surfaces and for detection of tissue-bound peptide-PEG conjugates.

This invention represents a new and simple approach to direct conjugation of polymers, peptides, proteins, biomolecules and/or a range of therapeutic agents to tissue surfaces. Illustrating several non-limiting embodiments, this invention utilizes a bifunctional molecule and a biological enzyme (e.g., a tTG), as can be pharmaceutically formulated in an aqueous solution or another suitable medium. The bifunctional molecule and enzyme solution is applied to or put in contact with a tissue surface, and the enzyme catalyzes the direct covalent coupling of the bifunctional molecule onto the tissue surface, and/or with proteins contained within the extracellular matrix of the tissue.

tTG is widely distributed within many connective tissues and has been implicated in organogenesis, tissue repair and in tissue stabilization. Cartilage was chosen for purpose of initial demonstration in part because a prior study showed that cartilage tissue surfaces adhered strongly to each other when incubated with tTG enzyme, suggesting a high level of reactivity of cartilage ECM components as substrates for tTG. (Jurgensen K, Aeschlimann D, Cavin V, Genge M, and Hunziker E. A new biological glue for cartilage-cartilage interfaces: tissue transglutaminase. Journal of Bone and Joint Surgery 1997; 79-A: 185-193.) In fact, several components of the cartilage ECM have been identified as substrates for tTG, including osteopontin, collagen II, collagen XI, fibrillin, fibronectin, and osteonectin. See, e.g., Prince C, Dickie D, and Krumdieck C. Osteopontin, a substrate for transglutaminase. Biochemical and Biophysical Research Communication 1991; 177: 1205-1210; Sorensen E, Rasmussen L, Moller L, Jensen P, Hojrup P, and Petersen T. Localization of transglutaminase-reactive glutamine residues in bovine osteopontin. Biochemical Journal 1994; 304: 13-16; Aeschlimann D, Wetterwald A, Fleisch H, and Paulsson M. Expression of tissue transglutaminase in skeletal tissues correlates with events of terminal differentiation of chondrocytes. Journal of Cell Biology 1993; 120: 1461-1470; Aeschlimann D, Kaupp O, and Paulsson M. Transglutaminase-catalyzed matrix crosslinking in differentiating cartilage: identification of osteonectin as a major glutaminyl substrate. Journal of Cell Biology 1995; 129: 881-892; Kleman J P, Aeschlimann D, Paulsson M, and Vanderrest M. Transglutaminase-catalyzed cross-linking of fibrils of collagen V/Xi in A204 rhabdomyosarcoma cells. Biochemistry 1995; 34: 13768-13775; Raghunath M, Cankay R, Kubitscheck U, Fauteck J D, Mayne R, Aeschlimann D, et al. Transglutaminase activity in the eye: Cross-linking in epithelia and connective tissue structures. Investigative Ophthalmology & Visual Science 1999; 40: 2780-2787; Fesus L, Metsis M L, Muszbek L, and Kotelian-sky V E. Transglutaminase-sensitive glutamine residues of human-plasma fibronectin revealed by studying its proteolytic fragments. European Journal of Biochemistry 1986; 154: 371-37; and Hohenadl C, Mann K, Mayer U, Timpl R, Paulsson M, and Aeschlimann D. Two adjacent N-terminal glutamines of BM-40 (osteonectin, SPARC) act as amine acceptor sites in transglutaminase-catalyzed modification. Journal of Biological Chemistry 1995; 270: 23415-20.

Other known ECM substrates of tTG found in other tissues include collagen I, collagen V, vitronectin, and laminin. (See, Chau D Y S, Collighan R J, Verderio E A M, Addy V L, and Griffin M. The cellular response to transglutaminase-cross-linked collagen. Biomaterials 2005; 26: 6518-6529; Orban J M, Wilson L B, Kofroth J A, El-Kurdi M S, Maul T M, and Vorp D A. Crosslinking of collagen gels by transglutaminase. Journal of Biomedical Materials Research Part A 2004; 68A: 756-762; Kleman J P, Aeschlimann D, Paulsson M, and Vanderrest M. Transglutaminase-catalyzed cross-linking of fibrils of collagen V/Xi in A204 rhabdomyosarcoma cells. Biochemistry 1995; 34: 13768-13775; Sane D C, Moser T L, Parker C J, Seiffert D, Loskutoff D J, and Greenberg C S. Highly sulfated glycosaminoglycans augment the cross-linking of vitronectin by guinea-pig liver transglutaminase-functional-studies of the cross-linked vitronectin multimers. Journal of Biological Chemistry 1990; 265: 3543-3548. Skorstengaard K, Halkier T, Hojrup P, and Mosher D. Sequence location of a putative transglutaminase cross-linking site in human vitronectin. FEBS Letters 1990; 262: 269-274; and Aeschlimann D, Paulsson M, and Mann K. Identification of Gln(726) in nidogen as the amine acceptor in transglutaminase-catalyzed cross linking of laminin-nidogen complexes. Journal of Biological Chemistry 1992; 267: 11316-11321.)

Transglutaminases (TG, protein-glutamine:amine γ-glutamyltransferase, e.g., EC 2.3.2.13) are calcium-dependent enzymes that catalyze a posttranslational acyl-transfer reaction between the γ-carboxamide groups of peptide-bound glutamine residues and the ε-amino groups of lysine residues in proteins, or certain primary amino groups. This reaction results in the formation of ε-(γ-glutamyl)lysine isopeptide side-chain bridges. TG reactions involve two substrates: lysine substrate and glutamine substrate (Scheme 1). The substrate specificity of lysine substrate and glutamine substrate were recently optimized using short peptides by rational design and combinatorial methods. Here, optimized substrate peptides are covalently conjugated to a bioactive and/or therapeutic agent. Solutions of these molecules in the presence of TG enzyme can then be applied to a recipient tissue surface where the TG enzyme catalyzes the covalent attachment of active molecule/agent to the tissue. Accordingly, this invention provides a biocompatible and simple approach to tissue modification, one which can be implemented with any appropriate tissue or on any tissue surface.

fully understood, although it is believed that the enzyme has more stringent requirements for the glutamine (acyl donor) than for the lysine (amine donor) Recent combinatorial library studies suggest that the amino acid directly adjacent to the reactive glutamine is not as important as the amino acids 2-3 residues away on the C-terminus side. Proline and phenylalanine as well as other nonpolar amino acids have been suggested to have favorable roles in those locations. In contrast, tTG is considered more tolerant of lysine substrates, as

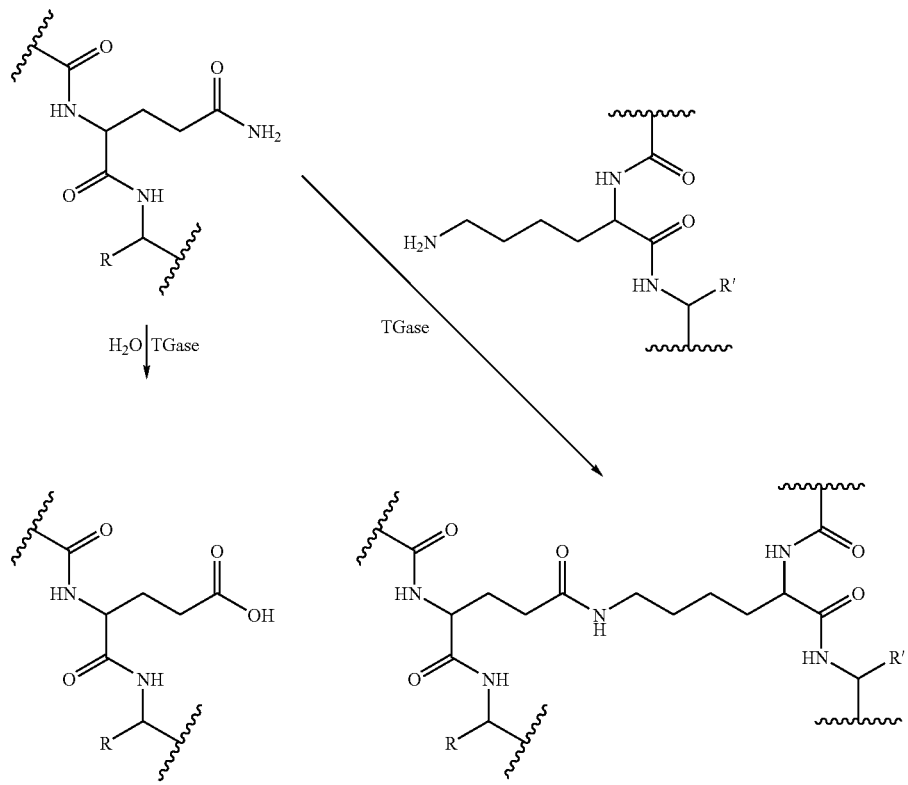

Scheme 1 Transglutaminase Catalyzed Reactions

A suitable bifunctional molecule can include a peptide containing either a lysine or glutamine amino acid residue or moiety and is preferably a short peptide of six residues or less. The peptide is coupled to a bioactive agent; that is, a molecule which can be a synthetic polymer, a biomolecule (e.g., protein, biologically active peptide, oligosaccharide or polysaccharide, DNA, RNA, antibody, etc.), and/or an agent such as drug, prodrug, or other active component, such as a molecule, agent and/or component that imparts a therapeutic, physiological and/or reparative effect to a tissue. Thus, the approach is modular, includes all combinations of lysinyl/glutaminyl peptide substrates and bioactive agents possible and is limited only by synthetic technique sufficient to couple or conjugate such components.

To demonstrate the general approach of tissue surface modification using tTG enzymes, a simple and versatile molecular module was designed consisting a relatively short synthetic peptide substrate that could ultimately be conjugated to a therapeutic molecule such as a peptide, protein, growth factor, drug or synthetic polymer. Specific requirements for tTG reactive glutamine and lysine residues are not it has been found to react with a wide variety of primary amines as well as peptide bound lysines. Nevertheless, certain peptide features do influence lysine reactivity, such as the presence of a C-terminal adjacent glycine or an N-terminal hydrophobic residue juxtaposed to lysine.

The lysine and glutamine-containing peptides used herein were rationally designed, taking such factors into consideration, and shown to be tTG substrates. For instance, both FKG-NH$_2$ and GQQQLG (SEQ ID NO: 1)-NH$_2$ bind to cartilage surfaces via tTG as demonstrated by tissue staining experiments. Various other lysinyl and glutaminyl substrates and sequences useful in the present context would be understood by those skilled in the art made aware of this invention. For instance, numerous glutamine and lysine-containing peptides/sequences (e.g., PQQQYV (SEQ ID NO: 2)) were identified in Hu et at. Method for Screening and MALDI-TOF MS Sequencing of Encoded Combinatorial Libraries. Anal. Chem. 2007, 79, 7275-7285, the entirety of which is incorporated herein by reference. Further, conjugates of these peptides with 3.4 kDa PEG were similarly active, suggesting that the presence of the polymer had little effect on the ability of tTG to catalyze the coupling of the peptide to the tissue surface. (FIG. 1) Diffuse staining over the cartilage matrix as well as more intense focal staining in the pericellular region were observed (FIG. 2). The intense staining in the pericellular regions could be explained by tTG reactive noncollagenous proteins which are believed to mediate the interaction between cells and the ECM and can be found predominantly in the areas surrounding the chondrocytes. It is known that some noncollagenous cartilage ECM proteins, such as fibronectin, react well with tTG and therefore it was anticipated that the aforementioned peptides would react with the proteins in this region. Intense staining at the articular surface may be due to the high concentration of collagen there. Several representative peptide conjugates used to demonstrate this invention are listed in Table 1, below.

TABLE 1

Structures, abbreviations and mass analyses for synthetic peptide conjugates used in this study.

| Structure of peptide-PEG | Abbreviation | Expected Mass* (Da) | Observed Mass* (Da) |
|---|---|---|---|
| Biotin-(EO)$_2$-FKG-NH$_2$ | B2K | 894.08 | 893.49 |
| Biotin-(EO)$_2$-GQQQLG-NH$_2$ | B2Q | 1173.34 | 1172.57 |
| Biotin-(EO)$_2$-FOG-NH$_2$ | B2O | 880.05 | 879.50 |
| Biotin-(EO)$_2$-GNNNLG-NH$_2$ | B2N | 1131.26 | 1131.95 |
| Biotin-PEG-G-NH$_2$ | B72 | 3600 | 3600 |
| Biotin-PEG-FKG-NH$_2$ | B72K | 3800 | 3800 |
| Biotin-PEG-GQQQLG-NH$_2$ | B72Q | 4100 | 4100 |

*values shown for B72, B72K and B72Q are average mass values for polydisperse molecules.

Peptide conjugates were bound to ECM to a depth of approximately 8-13 microns from the cut tissue surface. The depth of tissue modification can be affected by many factors, including the ability of the enzyme and peptide reactants to diffuse into the tissue before reacting with ECM components. No difference was found for the depth of modification when lysine (B2K) or glutamine (B2Q) peptides were coupled to a 3.4 kDa PEG (B72K and B72Q, respectively), suggesting that the diffusion of the peptide components through the tissue is unlikely to be a limiting factor. The masses of all peptide conjugates are well below that of tTG (77 kDa), suggesting that diffusion of tTG may be a limiting factor. The surface coupling reaction did not require pretreatment of the tissue with chondroitinase, although the depth of tissue modification was greater when the tissue was partially digested. Deeper tissue modification, if desired, may be achieved with a higher concentration of chondroitinase, longer digestion times, or through the use of a different enzyme such as collagenase or hyaluronidase.

To correlate the observed tissue modification to specific matrix components of the tissue, tTG reactions were also conducted in solution using selected cartilage ECM proteins and the peptides. One of the major ECM components of cartilage is collagen II, which can be found throughout the cartilage matrix. Collagen II used in these studies was isolated by pepsin digestion, which yields primarily the triple helical region of collagen II. Both lysine peptide conjugates, B2K and B72K, were reactive toward collagen II, suggesting that glutamine residues in the triple helical region act as substrates for tTG. The B2Q and B72Q containing peptides were less reactive toward collagen II in solution, which could be due to loss of lysine residues as a result of hydroxylation during collagen II interchain crosslinking and glycosylation.

B2K and B72K were significantly (p<0.05) more reactive than B2Q and B72Q with all proteins except osteopontin. There are a few possible explanations for these results. First, FKG has a significantly higher specificity (560 mM$^{-1}$ min$^{-1}$) than GQQQLG (SEQ ID NO: 1) (34.1 mM$^{-1}$ min$^{-1}$), indicating that the amine donor (FKG) is more reactive with the enzyme than the acyl donor (GQQQLG (SEQ ID NO: 1)). (See, Hu B and Messersmith P. Rational design of transglutaminase substrate peptides for rapid enzymatic formation of hydrogels. Journal of the American Chemical Society 2003; 125: 14298-14299.) However, the reactivities of the glutamine and lysine residues in the ECM proteins may also play important roles and could explain the higher reactivity of osteopontin toward the glutamine peptide conjugates (B2Q and B72Q). In addition, unlike short peptide constructs that are expected to have no secondary or tertiary structure, the existence of alpha helices, beta sheets and higher order protein structures of proteins may shield some lysine and glutamine residues from the enzyme. For example, it has been demonstrated that when fibronectin is exposed to tTG and [$^{14}$C]putrescine in solution 4 glutamines are reactive. However, after partial digestion, as many as 8-9 glutamines were reactive toward tTG. Thus, the total number of lysine and glutamine residues in an ECM protein may not always be a reliable indicator of potential reactivity toward tTG.

As previously discussed, glucocorticoids provide relief from the pain and inflammation associated with OA by inhibiting IL-1, a potent inflammatory cytokine, and one embodiment of this invention can be used for localized drug delivery to tissues by covalently coupling a hydrocortisone prodrug to tissue surfaces via tissue transglutaminase. By covalently coupling the prodrug to the tissue surface, it is not subject to the joint fluid turnover which could remove drugs nonspecifically bound to the tissue. Accordingly, for reasons outlined above, the lysine substrate peptide was selected to be conjugated to hydrocortisone because the articular surface of cartilage is composed primarily of collagen II, which is readily crosslinked to lysine substrates in the presence of tTG. Considering the low solubility of hydrocortisone, a lysine substrate peptide was expected to enhance solubility of hydrocortisone in aqueous solutions. The molecular design of this particular TRIP-C included a hydrolysable ester linkage or coupling component between hydrocortisone and FKG peptide, allowing the drug to be released from the tissue surface under physiological conditions.

Despite evidence of being hydrolyzed in solution (Table 2, below), TRIP-C was coupled to the articular surface of cartilage via tTG and was detected within 30 µm of the articular surface. The kinetics of TRIP-C immobilization and the dependence on concentration were consistent with an enzyme-mediated reaction. For example, at low TRIP-C concentrations (0.1 and 1.0 mM), the amount of prodrug coupled was concentration dependent. However, at concentrations of 1.0 mM and greater, the amount of prodrug coupled was limited by $k_{cat}$ of the enzyme, as evidenced by a constant amount of bound prodrug despite an increase in concentration. The quantity of prodrug coupled to the articular surface also increased with incubation time and was likely limited by the hydrolytic stability of the prodrug, by the stability of the enzyme, and by competition with hydrolyzed FKG peptide, which remained a substrate of the enzyme. Because the immobilization of the prodrug was enzyme-mediated, it may be possible for more prodrug to be coupled with an increase in enzyme concentration.

The hydrolysis of hydrocortisone from TRIP-C immobilized on the articular surface was examined in Buffer 1, normal bovine synovial fluid, and human osteoarthritic synovial fluid. In both Buffer 1 and normal synovial fluid, the rate of release of hydrocortisone from the cartilage surface into the fluid was less than the rate of solution hydrolysis of the prodrug in the corresponding fluid. This suggests that immobilization of the prodrug onto the tissue via chemical production of an amide bond eliminated the intramolecular catalytic cleavage of the ester, facilitated by the amine group on lysine, and decreased hydrolysis. In addition, the presence of esterases in the synovial fluids were likely responsible for increased prodrug hydrolysis in both solution and on the cartilage surface over that observed in Buffer 1. The lifetime of the prodrug can be increased by altering the sequence and length of the peptide. These changes can potentially influence the ability of esterases to hydrolyze the ester bond. Furthermore, because tTG has a broad substrate specificity for the lysine peptide, a peptide other than FKG may provide more steric inhibition to the intramolecular hydrolysis, while still retaining acceptable levels of reactivity with tTG. While there was an increase in hydrolysis of TRIP-C in the synovial fluids as compared to Buffer 1 due to the presence of esterases, there was no detectable difference between the normal and osteoarthritic synovial fluids. This could be related to the amount of prodrug on the surface, which may have been too small to detect a difference in the rate of hydrolysis between treatments. It is also possible that the esterases from bovine and human sources have different activities. It has been shown that the source of esterases even from different organs within the same animal, may exhibit variable rates of hydrolysis. In order to increase the lifetime of the prodrug on the surface, the addition of hyaluronic acid to the incubating solution could increase the viscosity of the solution and reduce hydrolysis, likely because of decreased enzyme mobility.

Alternatively, consider that PEG has been used previously to camouflage proteins from circulating enzymes and immune cells, and has also been used to make biological surfaces inert to protein deposition and cell adhesion. In addition, it was previously demonstrated that the addition of PEG does not adversely affect enzyme action. Therefore, it was hypothesized that the PEG in TRIP-PC may provide protection for hydrocortisone from hydrolytic enzymes in synovial fluid after coupling to the articular surface. However, at least under the conditions employed, while modification of the prodrug with PEG did not adversely affect its coupling to tissue, there was no difference in hydrocortisone hydrolysis from TRIP-C or TRIP-PC coupled to the articular surface in any of the fluids utilized. This could be due to the length of the PEG, which may not properly cover the articular surface. In addition, the epitopes to which the peptide binds on the articular surface may not be close together and hence coverage of the cartilage is insufficient. The use of a longer PEG, such as 10 kDa to 40 kDa, may provide better coverage and hence reduce hydrolysis.

The articular surface of cartilage is only one joint structure to which the prodrug would be coupled via tTG if injected intra-articularly. TRIP-C in the joint space could in principle be used to modify any tissue bathed in synovial fluid, provided the tissue is composed of tTG substrates such as collagen I, collagen II, collagen XI, fibronectin, vitronectin, and laminin. An example is the meniscus, a fibrocartilage tissue of the knee located between the articulating surfaces of the femur and tibia. As shown in FIG. 7, TRIP-C was successfully immobilized on meniscal tissue, similar to the articular surface of cartilage. The outer portion of the meniscus is primarily composed of collagen I, which is also a substrate of tTG, while the composition of the inner portion of the meniscus is composed primarily of collagen II, similar to the articular surface. The increased amount of TRIP-C bound on the meniscal surface as compared to cartilage can be due to the combination of the fibrous structure creating more surface area and the difference on composition. It is also expected that the synovial lining which covers many joint structures such as ligaments will also be modified with the prodrug in vivo since they are also composed of collagen I.

With respect to the compounds, compositions and/or methods of the present invention, the aforementioned substrates, agents and components can comprise, consist of, or consist essentially of any of the aforementioned sequences, residues, drugs, prodrugs, moieties, components, substituents and functional groups thereof. Each such compound, peptide/sequence/residue, agent, component or moiety/substituent thereof is distinguishable, characteristically contrasted, and can be practiced in conjunction with the present invention separate and apart from another. Accordingly, it should be understood that the inventive compounds, compositions and/or methods, as illustratively disclosed herein, can be practiced or utilized in the absence of any one enzyme compound, agent, peptide, sequence, moiety and/or substituent which may or may not be disclosed, referenced or inferred herein, the absence of which may or may not be specifically disclosed, referenced or inferred herein.

The compounds of this invention may contain an acidic or basic functional group and are, thus, capable of forming pharmaceutically-acceptable salts with pharmaceutically-acceptable acids and bases. The term "pharmaceutically-acceptable salts" refers to the relatively non-toxic, inorganic and organic acid and base addition salts of such compounds. These salts can be prepared by reacting the purified compound with a suitable acid or base. Suitable bases include the hydroxide, carbonate or bicarbonate of a pharmaceutically-acceptable metal cation, ammonia, or a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

A tissue condition or disease state can be treated by contacting a tissue with an effective amount of an inventive compound. The contacting may take place in vitro or in vivo. "Contacting" means that a tissue and such a compound are brought together so that the compound can bind to the tissue. Amounts of a compound effective for tissue treatment may be determined empirically, and making such determinations is within the skill in the art.

To treat an animal/subject, an effective amount of one or more of the present compounds or a pharmaceutically-acceptable salt thereof can be administered. Effective dosage forms, modes of administration and dosage amounts may be determined empirically, and making such determinations is within the skill of the art. It is understood by those skilled in the art that the dosage amount will vary with the activity of the particular compound employed, a particular tissue, tissue condition or disease state, the route of administration, the rate of excretion of the compound, the duration of the treatment, the identity of any other drugs being administered to the animal/subject, the age, size and species of the animal, and like factors well known in the medical and veterinary arts. In general, a suitable daily dose will be that amount which is the lowest dose effective to produce a therapeutic effect. The total daily dosage will be determined by an attending physician or veterinarian within the scope of sound medical judgment. If desired, the effective daily dose of such a compound, or a pharmaceutically-acceptable salt thereof, maybe administered as two, three, four, five, six or more sub-doses, administered separately at appropriate intervals throughout the day. Treatment according to the invention, includes mitigation, as well as elimination, of the tissue or condition or disease state. Animals treatable according to the invention include mammals. Mammals treatable according to the invention include dogs, cats, other domestic animals, and humans.

Compounds of this invention may be administered to an animal/patient for therapy by any suitable route of tissue administration, including articularly or to or by a joint tissue or tissue associated with a joint. While it is possible for the compound(s) (one or more compounds of this invention and/or pharmaceutically-acceptable salts thereof) to be administered alone, it can be preferable to administer the compound(s) as a pharmaceutical formulation (composition). The pharmaceutical compositions of the invention comprise the compound(s) in admixture with one or more pharmaceutically-acceptable carriers and, optionally, with one or more other compounds, drugs or other materials. Each carrier must be "acceptable" in the sense of being compatible with the other ingredients of the formulation and not injurious to the patient. Pharmaceutical formulations of the present invention include those suitable for tissue, articular and/or intra joint administration. Regardless of the route of administration selected, the compound(s) are formulated into pharmaceutically-acceptable dosage forms by conventional methods known to those of skill in the art.

The amount of the compound(s) which will be combined with a carrier material to produce a single dosage form will vary depending upon the host being treated, the particular mode of administration and all of the other factors described above. The amount of the compound(s) which will be combined with a carrier material to produce a single dosage form will generally be that amount of the compound(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both.

Formulations of the invention suitable for tissue administration may be in the form of a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as a gel, each containing a predetermined amount of the compound(s). Liquid dosage forms for tissue administration of the compound(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers. Besides inert diluents, the compositions can also include adjuvants such as buffers, esterases, transglutaminases wetting agents, emulsifying and suspending agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof. Proper fluidity can be maintained, for example, by the use of coating materials, such as lecithin or by the maintenance of the required particle size in the case of dispersions, and by the use of surfactants.

These compositions may also contain adjuvants such as isotonic agents, such as sodium chloride and the like. In addition, effect of an injectable pharmaceutical form may be brought about by the inclusion of agents which promote or delay release or delivery of a bioactive agent.

EXAMPLES OF THE INVENTION

The following non-limiting examples and data illustrate various aspects and features relating to the compounds, compositions and/or methods of the present invention, including the delivery of various bioactive agents using tissue-targeted peptide conjugates, as are available through the synthetic methodologies described herein. In comparison with the prior art, the present compounds, compositions and/or methods provide results and data which are surprising, unexpected and contrary thereto. While the utility of this invention is illustrated through the use of several bioactive agents and peptide components which can be coupled thereto, it will be understood by those skilled in the art that comparable results are obtainable with various other compounds or compositions, and the bioactive agents and peptide components thereof, as are commensurate with the scope of this invention.

Materials

Rink amide resin was purchased from Anaspec, San Jose, Calif. Fmoc-amino acids were purchased from Peptides International, Louisville, Ky. O—(N-Fmoc-3-aminopropyl)-O'-(N-diglycolyl-3-aminopropyl)-diethyleneglycol (MW 558.6) (Fmoc-NH-(EO)$_2$—COOH) was purchased from Novabiochem, San Diego, Calif. and Fmoc-NH-PEG-NHS ($\overline{M}_w$=3.4 kDa) was purchased from Nektar Therapeutics, Inc, Huntsville, Ala. Biotin, guinea pig liver tissue transglutaminase (tTG), chondroitinase ABC, fibronectin, and peroxidase conjugated ExtrAvidin were purchased from Sigma, St. Louis, Mo. Adult bovine metacarpophalangeal joints were purchased from a local slaughter house. Fluorescein and peroxidase conjugated anti-biotin antibodies and the DAB substrate kit were purchased from Vector Labs, Burlingame, Calif. Anti-Collagen II and Texas Red conjugated donkey anti-rabbit antibodies were purchased from Abcam, Cambridge, Mass. Collagen II was purchased from Chondrex, Redmond, Wash., osteonectin from Biodesign, Saco, Me., and osteopontin from R&D Systems, Minneapolis, Minn. ECL Plus western blotting detection reagents were purchased from GE Healthcare Biosciences, Piscataway, N.J.

Applicable to examples 12-23, H-Gly-2-ClTrt-Resin was purchased from Peptides International, Louisville, Ky. All Fmoc-Amino acids, anti-hydrocortisone antibody, and fluorescein conjugated goat anti-mouse secondary antibody were purchased from EMD Biosciences, San Diego, Calif. mPEG amine ($\overline{M}_w$=5.0 kDa) was purchased from Nektar Therapeutics, Inc, Huntsville, Ala. Hydrocortisone 21-hemisuccinate, 6α-methyl-prednisolone, DEAE cellulose, and papain were purchased from Sigma, St. Louis, Mo. Twenty-two week-old bovine knees were purchased from a local slaughter house. Phosphate buffered saline was purchased from Invitrogen, Carlsbad, Calif. Goat serum was purchased from Abcam, Cambridge, Mass. Complete Mini protease inhibitor tablets was purchased from Roche Applied Science, Indianapolis, Ind. Cortisol Parameter Assay kit was purchased from R&D Systems, Minneapolis, Minn. Guinea pig livers were purchased from Charles River, Wilmington, Mass. from which tTG was isolated and the activity determined as described in the literature. Bovine synovial fluid was purchased from Animal Technology, Tyler, Tex. Human osteoarthritic synovial fluid was a gift from Dr. James Williams, Rush University, Chicago, Ill.

Example 1a

Synthesis of Peptide Conjugates

The molecules synthesized to demonstrate this invention, for use in this and their abbreviations, are listed in Table 1, above. The peptide portions of the molecules were synthesized on a Rink amide resin (1 g, 0.45 mmol/g) using standard Fmoc solid phase peptide synthesis. Each coupling reaction was performed for 3 hours with a 10 min pre-activation of four equivalents of Fmoc-amino acid:benzotriazole-1-yloxy-tris(dimethylamino)-phosphoniumhexafluorophosphate (BOP):N-hydroxybenzotriazole (HOBt):diisopropylethylamine (DIEA) (1:1:1:1) at room temperature. The Fmoc was removed by 20% piperidine in N-methylpyrrolidinone (NMP) for 1 hour. After Fmoc removal from the final amino acid, either Fmoc-NH-(EO)$_2$—COOH or Fmoc-NH-PEG-NHS was added. Fmoc-NH-(EO)$_2$—COOH was treated as Fmoc-amino acid and used at 2 equivalents. The Fmoc-NH-PEG-NHS was used at 2 equivalents and combined with DIEA (1:2) in dichloromethane (DCM), added to the resin and reacted for 2 days. The unreacted peptide on the resin was acetylated with the use of 4 equivalents of acetic anhydride. The Fmoc was then removed and biotin was coupled using 4 equivalents by the previously described procedure for coupling Fmoc-amino acids. At the completion of the reaction, the resin was washed with NMP, DCM, and methanol (MeOH), two times each. The resin was dried under vacuum and then treated with 95% trifluoroacetic acid (TFA), 2.5% water, and 2.5% triisopropylsilane for 3 hours. The crude product was obtained by concentration of the TFA solution and addition of diethyl ether. Purification was performed using semi-preparative RP-HPLC and the masses were confirmed using MALDI-TOF MS analysis on a PE Voyager DE-Pro MALDI-TOF Mass Spectrometer (Perspective Biosystems, MA). The peptide-PEG conjugates were then frozen and lyophilized.

Example 1b

Cartilage Isolation and Preparation

For the coupling of peptide conjugates to cartilage sections, osteochondral plugs were extracted from adult bovine metacarpophalangeal joints using a hole punch with a diameter of 0.793 cm. Samples were then frozen in tissue freezing media and stored at −80° C. until use. Vertical sections (25 µm), which included the articular surface as well as a portion of the underlying bone, were cut using a cryostat (Microm HM505N, Carl Zeiss) and the freezing media was removed with 3 washes of Tris buffered saline (TBS) (50 mM Tris, 100 mM NaCl) at pH 7.4. For the penetration studies, four millimeter by two millimeter rectangular samples of cartilage were excised from adult bovine metacarpophalangeal joint to a depth of 200-250 microns from the articular surface. Samples were frozen as described earlier for later use, at which time they were thawed and rinsed in TBS.

Example 2

Coupling of Peptide Conjugates to Cartilage Sections

A general scheme of the covalent coupling of the peptide-PEG conjugates to cartilage is shown in FIG. 1. Partial depolymerization of glycosaminoglycans in the tissue was accomplished by digesting with chondroitinase ABC at 40 mU/mL in 50 mM Tris, 70 mM sodium acetate and 0.01% bovine serum albumin (BSA) at pH 8 for 30 minutes at 37° C. Samples were then rinsed 3 times with TBS and blocked with 1% BSA in TBS for one hour at room temperature. The tTG reaction conditions used were similar to a previously described method. (See, Aeschlimann D, Wetterwald A, Fleisch H, and Paulsson M. Expression of tissue transglutaminase in skeletal tissues correlates with events of terminal differentiation of chondrocytes. Journal of Cell Biology 1993; 120: 1461-1470.) The cartilage sections were incubated in 500 µL of 50 µM peptide or peptide-PEG conjugate, 0.5 U/mL tTG, 5 mM CaCl$_2$, 2.5 mM dithiothreitol and 100 mM Tris, at pH 8.3 for 30 min at 37° C. Control experiments were performed in the absence of tTG. After completion of the tTG reaction, the solution was removed and samples were rinsed 3 times with 1% BSA in TBS for 5 minutes each. The cartilage sections were then incubated with fluorescein conjugated anti-biotin antibody at 10 µg/mL in 1% BSA in TBS for 2 hours at room temperature. Samples were rinsed 4 times with TBS for 5 minutes each, followed by blocking with 10% donkey serum for 1 hour and incubation with rabbit anti-collagen II antibody in TBS containing 10% donkey serum for 1 hour. The samples were rinsed 3 times with 10% donkey serum in TBS and then incubated with Texas Red conjugated donkey anti-rabbit antibody. Samples were rinsed again with TBS and then imaged using a Leica epifluorescent microscope ($\lambda_{ex}$=495 nm, $\lambda_{em}$=520 for fluorescein and $\lambda_{ex}$=596 nm, $\lambda_{em}$=620 for Texas Red) and a SPOT RT digital camera (Diagnostic Instruments, Sterling Heights, Mich.).

Example 3

Image Analysis

Images were analyzed using Metamorph image analysis software (Molecular Devices, Sunnyvale, Calif.). Fluorescein fluorescence was measured at three randomly selected areas of the middle zone on each cartilage section image and then averaged. A similar procedure was utilized to determine Texas Red fluorescence. The fluorescein fluorescence intensity was then normalized to the fluorescence of the Texas Red for each cartilage section image in order to account for potential ECM differences between sections. Finally, the average green fluorescence for each peptide-PEG conjugate was then normalized by dividing by the red fluorescence.

Example 4a

Depth of Peptide Coupling in Cartilage

Figure 6:
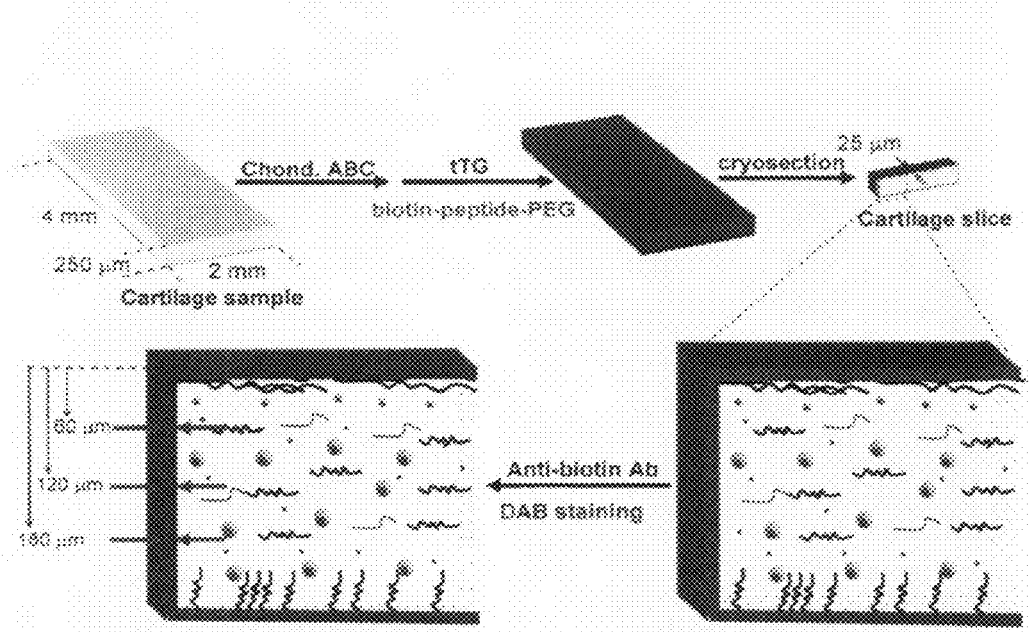
FIG. 6. Schematic illustration of the method used for determination of depth of peptide coupling to cartilage. A 4 mm by 2 mm by 0.25 mm piece of cartilage was treated with Chondroitinase ABC and then reacted with tTG and biotinylated peptide-PEG. After cryosectioning the slice was treated with anti-biotin antibody followed by DAB staining through a secondary antibody. The thickness of DAB staining was measured at 60, 120 and 180 μm from the articular surface as indicated by the blue arrows.

Four millimeter by two millimeter rectangular samples of cartilage were thawed and rinsed, after which the chondroitinase ABC digestion and tTG reactions with the peptide and peptide-PEG conjugates were performed as stated above. (See FIG. 6 for schematic of this experimental method.) After the tTG reaction, the cartilage was removed and rinsed 3 times with TBS for 5 minutes each. The samples were then frozen in tissue freezing media followed by cutting using a cryostat. Twenty micron thick vertical sections were collected from each cartilage piece, rinsed in TBS, blocked with 1% BSA TBS containing 0.1% Tween (TBST), and incubated with peroxidase conjugated anti-biotin antibody at 5 µg/mL in 1% BSA in TBS-T for 2 hours at room temperature. Samples were rinsed 4 times with TBS and 4 times with distilled water. Finally, the anti-biotin antibody was detected using a DAB kit which contains the peroxidase substrate 3,3'-diaminobenzidine yielding a brown color. Samples were imaged using a Leica microscope (brightfield) and a SPOT RT digital camera.

Example 4b

Adobe Photoshop (Adobe, Inc, San Jose, Calif.) was used to measure the depth to which the peptide and peptide-PEG conjugates were detected. The depth of staining into the cartilage along the cut surface perpendicular to the articular surface was measured at distances of 60, 120 and 180 microns from the articular surface for each sample. The average depth of staining for each sample was calculated from these three measurements. For each peptide and peptide-PEG conjugate, an overall mean depth of staining was determined from the measurements of three samples.

Example 5

Reaction of Peptides with Cartilage ECM Proteins

Fibronectin, collagen II, osteonectin, and osteopontin were separately combined at 0.1% (w/v) in 100 mM Tris and 5 mM $CaCl_2$ with 500 µM peptide-PEG conjugates and 0.05 U/mL tTG. The reaction was allowed to proceed for 30 min at 37° C. and then stopped with the addition of iodoacetamide (1 mM final concentration). Control experiments without transglutaminse were also performed. The proteins were then separated using SDS-PAGE with either 7.5% fibronectin and collagen II) or 10% (osteonectin and osteopontin) gels, transferred to PVDF membranes which were then blocked with 2% BSA in TBS with 0.1% Tween (TBS-T). The modified proteins were probed with peroxidase conjugated ExtrAvidin. Detection of bound ExtrAvidin was accomplished using ECL Plus Western Blotting Detection Reagents and imaged on a Storm 860 imager (GE Healthcare Biosciences, Piscataway, N.J.). Band intensities were measured using ImageQuant (GE Healthcare Biosciences). Statistical analysis was performed using one-way ANOVA and Tukey's post-hoc test with 95% confidence intervals with SPSS (SPSS, Chicago, Ill.). Reactions of B72Q and B72K with osteonectin and osteopontin were dialyzed against 10 mM acetic acid and then analyzed by MALDI-TOF MS.

Example 6a

In the presence of tTG enzyme, B2K, B2Q, B72K, and B72Q were enzymatically crosslinked to the cartilage sections as evidenced by the images of the tissue sections stained with fluorescein anti-biotin antibody (FIGS. A, D, G and H). Fluorescence was detected in all regions of the cartilage, from the articular surface to the calcified zone, although fluorescence intensity was greatest near the lacunae. The B2K and B72K treated samples qualitatively appeared to be more fluorescent than the B2Q and B72Q modified cartilage sections.

Example 6b

The catalytic role of tTG in coupling the peptide-PEG conjugates to cartilage was verified with several controls. First, incubation of B2K and B2Q with the cartilage in the absence of tTG resulted in no observed fluorescence (FIGS. 2B and E), indicating that tTG was required for the coupling of the peptide-PEG conjugates to cartilage. Secondly, when cartilage sections were incubated with B2N or B2O in the presence of tTG, no coupling was detected as evidenced by the lack of fluorescence in panels 2C and F. While asparagine and ornithine are structurally similar to glutamine and lysine, respectively, both are known to be poor substrates for tTG due to their shorter side chains. Finally, nonspecific binding of the biotin-PEG component of B72K and B72Q to the cartilage can be ruled out as shown by the lack of fluorescence when the cartilage sections were incubated with B72 and tTG (FIG. 2I).

Example 6c

Figure 3A:
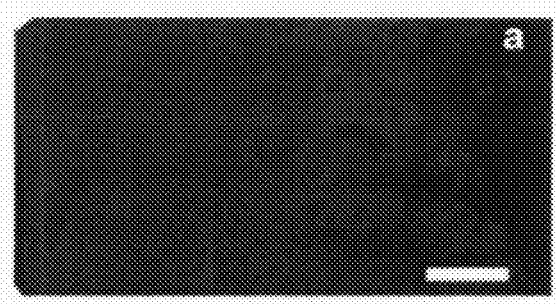
FIGS. 3A-C. Quantification of peptide-PEG coupled to cartilage. A) Typical Texas Red fluorescence digital image of untreated cartilage (the articular surface is shown at the left). Scale bar represents 25 μm. B) Texas Red fluorescence intensity of cartilage sections treated with the peptide-PEG conjugates and tTG. (C) Normalized fluorescein fluorescence intensity of the peptide-PEG treated cartilage. Error bars in B and C represent standard deviation.
Figure 3B:
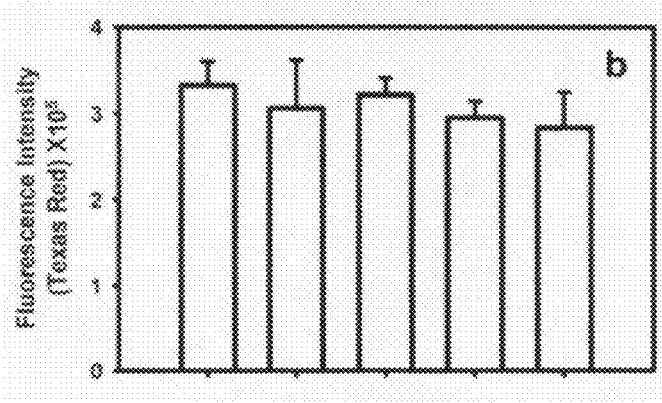
Figure 3C:
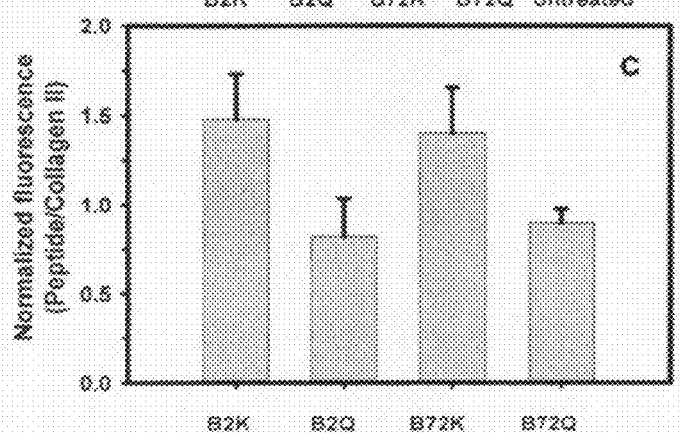

Texas Red staining of type II collagen proved to be a useful internal reference for quantifying bound peptide, as red fluorescence was detected in all regions of the cartilage (FIG. 3A) and was unaffected by the reaction with peptides and tTG enzyme as can be seen by the level of red fluorescence from the treated samples as compared to that of the untreated samples (FIG. 3B). This allowed the amount of peptide bound to the cartilage to be quantified by ratioing green fluorescence from the fluorescein conjugated anti-biotin antibody to that of the red fluorescence resulting from type II collagen staining. Although the average fluorescence intensity from bound peptide was more intense for B2K and B72K samples as compared to B2Q and B72Q samples (FIG. 3C), the differences were not statistically significant. The presence of a longer PEG linker did not significantly affect peptide coupling as the fluorescence of B2K and B72K and B2Q and B72Q were similar.

Example 7

Figure 4A:
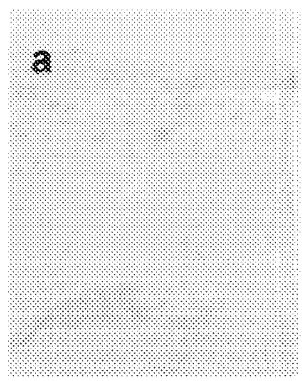
FIGS. 4A-C. Depth of peptide-PEG conjugation to cartilage as determined by DAB staining and image analysis. A) Representative digital image of cartilage treated with B72K peptide but no tTG. B) Representative digital image of cartilage treated with B2K peptide and tTG. Arrows indicate the region of the cartilage tissue near the exposed surface that has been stained with DAB. C) Graph comparing the thickness of tissue modified by the 4 peptide conjugates. Error bars represent standard deviation. The scale bar in (B) indicates 50 μm for both images.
Figure 4B:
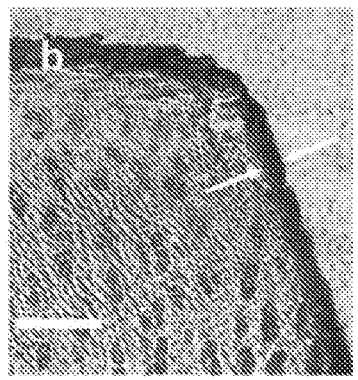
Figure 4C:
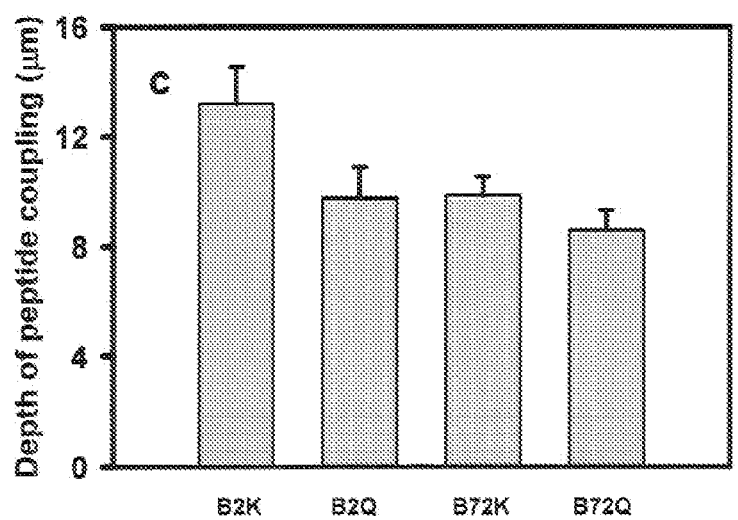

In a separate series of experiments, 2 mm by 4 mm by 200-250 µm pieces of cartilage were incubated with each peptide-PEG conjugate and tTG. At the completion of the reaction, the cartilage pieces were frozen and sectioned and the coupled peptide conjugates were detected with a perioxidase anti-biotin antibody. The bound antibody was detected with DAB reagent which forms a brown precipitate in the presence of perioxidase. A representative stained section is shown in FIG. 4B. The brown DAB staining was detected on the cut and articular surfaces as indicated by the arrows in FIG. 4B. The depth of peptide penetration and coupling was measured along the cut edge at 60, 120, and 180 µm from the articular surface as shown schematically in FIG. 6. No relationship was found between the thickness of DAB staining and distance from the articular surface. The average depth of peptide coupling for B2K was 13 µm. BQ2, B72Q, and B72K were detected at an average depth of 9.8 µm, 8.6 µm, and 9.8 µm, respectively (FIG. 4C). Statistical analysis indicated that the observed differences were not statistically significant. In the absence of tTG, no staining was observed (FIG. 4A). Finally, a control experiment in which undigested cartilage tissue was treated with tTG and B2K revealed staining to a depth of only 5.8 microns (data not shown), indicating that digestion with chondroitinase was not required but did enhance the depth of tissue modification.

Example 8

To identify components of the cartilage ECM that were reactive toward the peptide conjugates, enzyme reactions were conducted in solution with fibronectin, collagen II, osteonectin, and osteopontin. Coupling of peptide conjugates to all proteins was observed as evidenced by western blot analysis (FIG. 5A). With the exception of osteopontin, the cartilage proteins reacted more with lysine peptides (B2K and B72K) than with glutamine peptides (B2Q and B72Q) as evidenced by the amount of loaded protein required to detect the biotinylated conjugates. Preferential reactivity of the lysine peptides became evident when the band intensity was normalized by the amount of protein loaded (FIGS. 5B-E). For fibronectin, type II collagen, and osteonectin the normalized band intensity for B2K and B72K was statistically greater than for B2Q or B72Q ($p<0.05$). As observed with the tissue staining experiments, no differences were found between B2K and B72K and between B2Q and B72Q. For osteopontin, B2Q demonstrated a significantly greater normalized band intensity than the B2K and B72K ($p<0.05$). Control experiments without transglutaminase demonstrated that there were no non-specific interactions between the peptides and the proteins. In addition, reactions of the proteins with B2N, B2O and B72 in the presence of tTG did not demonstrate crosslinking on western blot (data not shown).

Example 9

Figure 7A:
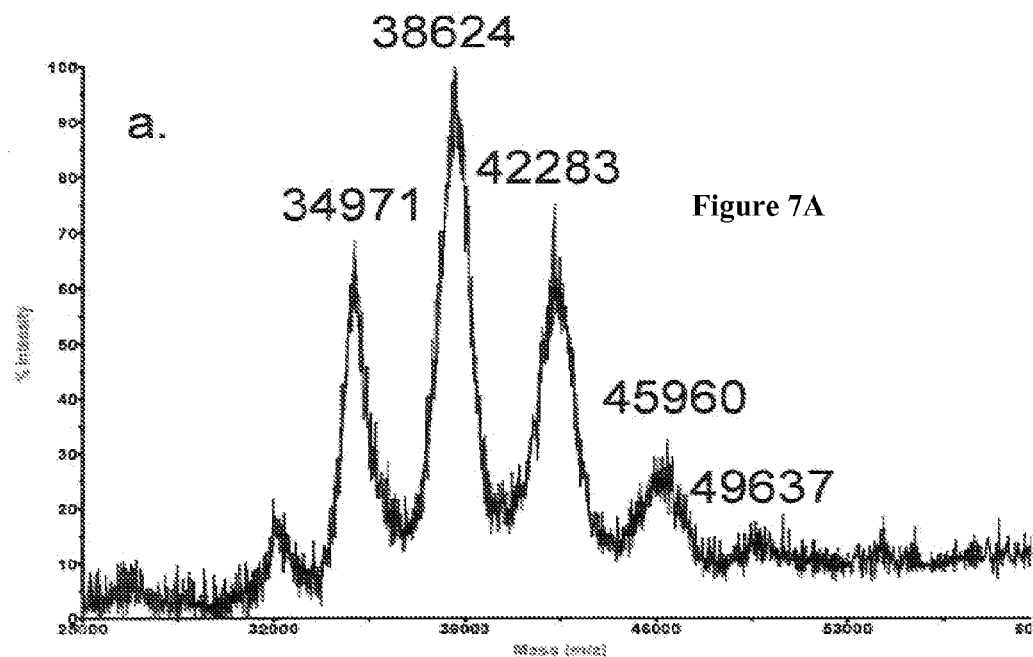
FIGS. 7A-B. MALDI-TOF MS spectra of osteonectin modified with PEG-peptides using tTG. A) Reaction with B72K. B) Reaction with B72Q. The peak at 34900 is the molecular ion peak of osteonectin. The difference in mass between peaks is approximately 4000 Da, the molecular weight of the peptide-PEG conjugates.
Figure 7B:
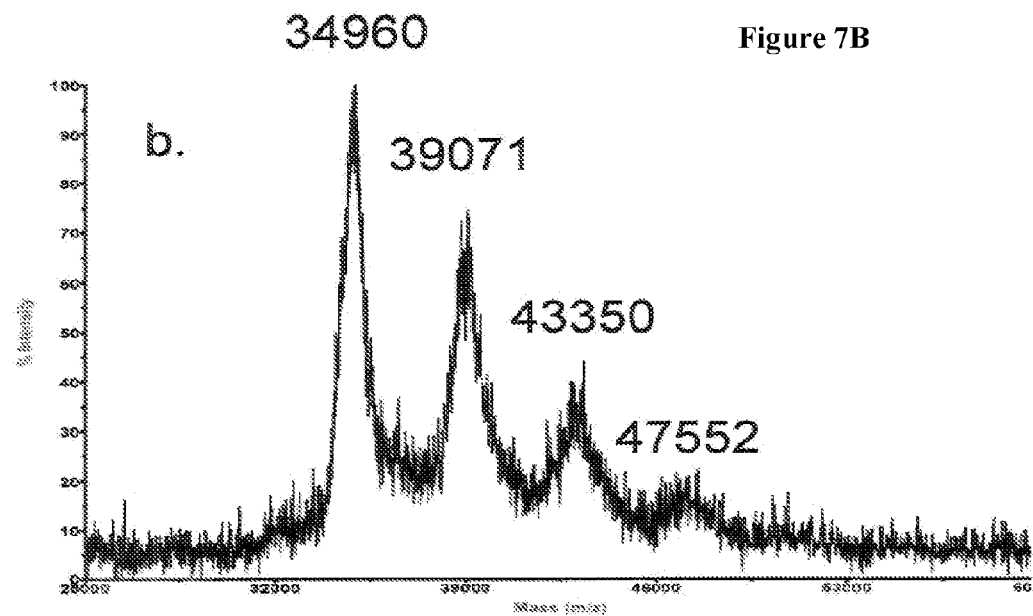
Figure 8A:
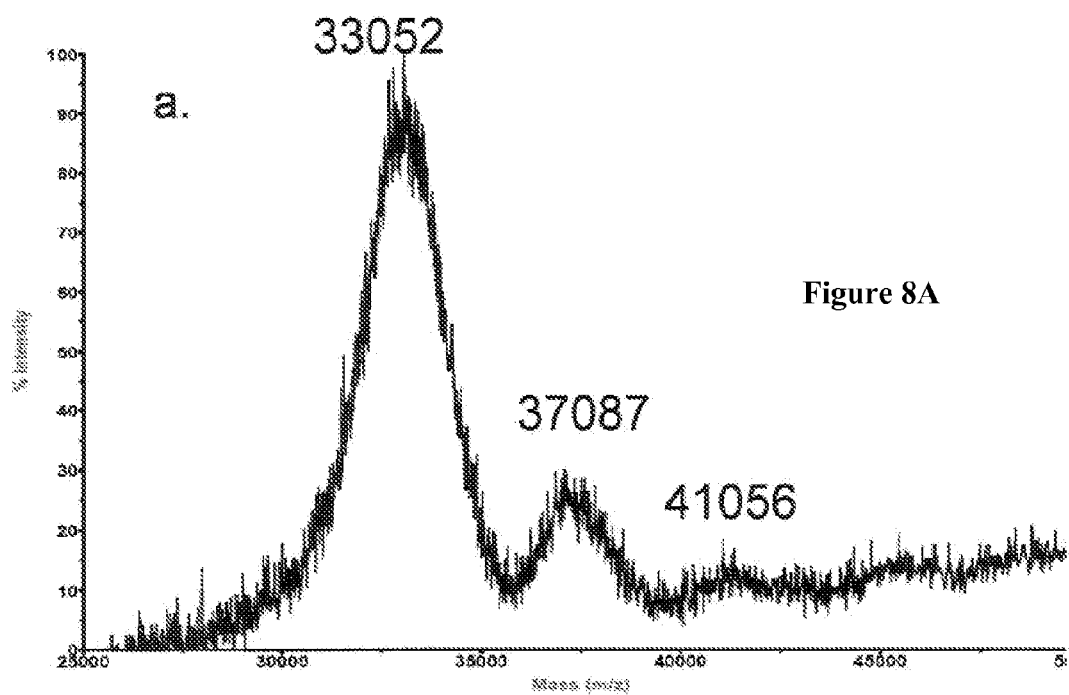
FIGS. 8A-B. MALDI-TOF MS spectra of osteopontin modified with PEG-peptides using tTG. A) Reaction with B72K. B) Reaction with B72Q. The peak at 33000 is the molecular ion peak of osteopontin. The difference in mass between peaks is approximately 4000 Da, the molecular weight of the peptide-PEG conjugates.
Figure 8B:
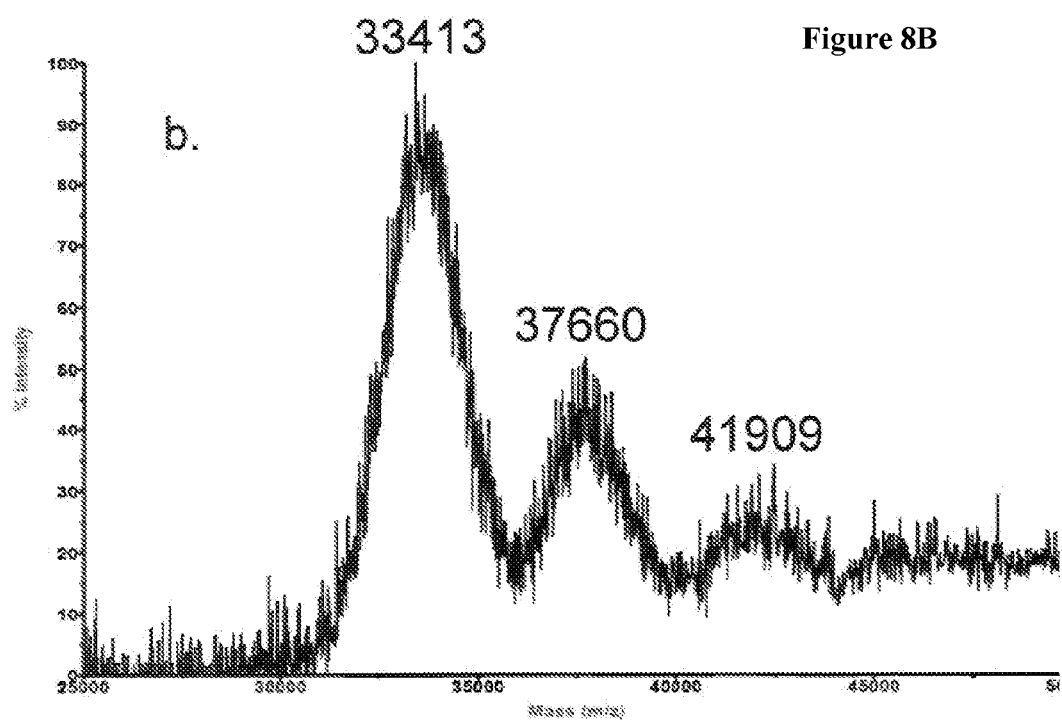

The MALDI-TOF spectrum of osteonectin modified with B72K demonstrated that the majority of the protein was modified with one PEG molecule although additional peaks corresponding to protein modified with up to 4 PEGs were detected (FIG. 7A). In contrast, when the spectrum of B72Q coupled osteonectin was evaluated, the peak corresponding to unmodified osteonectin was the most intense, indicating that a large portion of the protein had not been modified (FIG. 7B). There were also 3 additional peaks visualized, suggesting that osteonectin had been modified with up to 3 molecules of B72Q. The MALDI-TOF mass spectra of osteopontin revealed that majority of this protein was unmodified and that it had reacted with up to two B72Q while only reacting with one B72K (FIG. 8).

Example 10

Figure 9A:
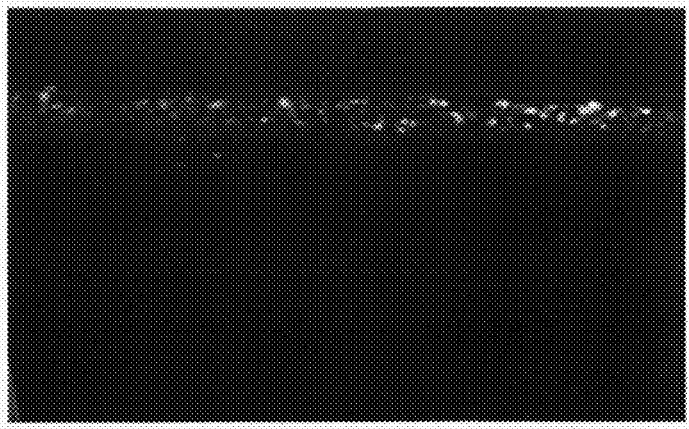
FIGS. 9A-C. Digital images of fluorescent anti-biotin antibody stained cartilage sections: A) without hyaluronan and without tTG; B) without tTG; and C) with hyaluronan and tTG.
Figure 9B:
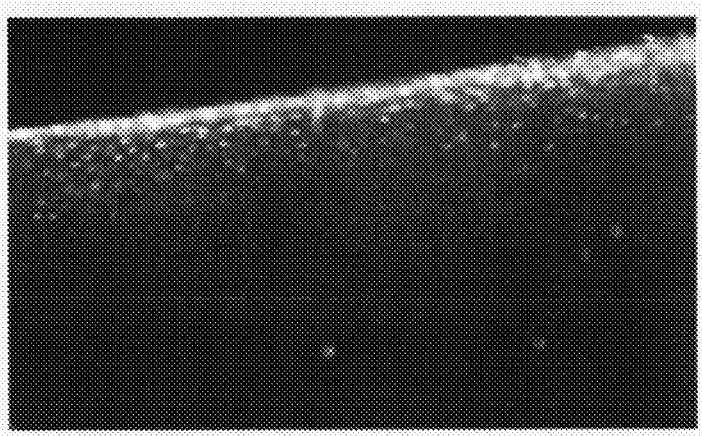
Figure 9C:
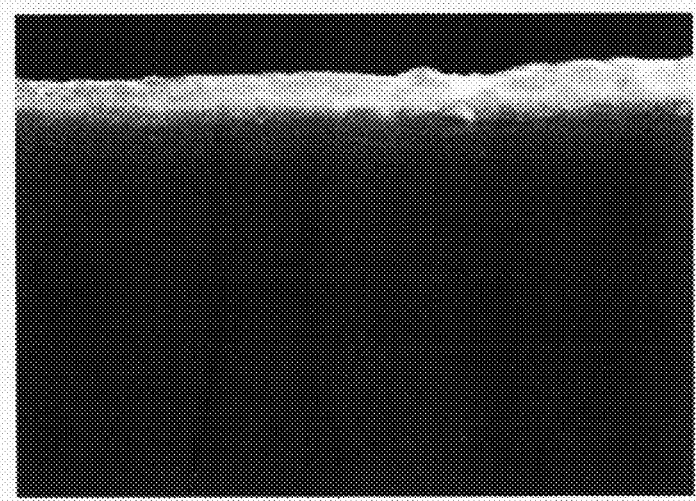

Fresh articular cartilage was modified with hyaluronan (HA) by exposing to a solution containing Biotin-FKG-HA (modification was 3.8% (using the HABA/Avidin assay). Controls included tissue modification with the bifunctional molecule in the absence of TG, and using peptide (Biotin-Ahx-FKG) without HA and without TG enzyme. The presence of molecule on the tissue surface was detected using an anti-biotin antibody. Only the bifunctional molecule incubated with tissue in the presence of enzyme revealed intense staining. (See, FIGS. 9A-C.)

Example 11

Figure 10A:
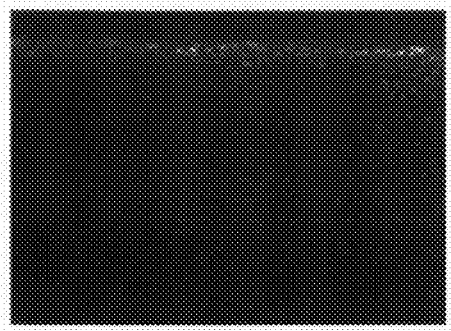
FIGS. 10A-C. Digital images of fluorescent anti-hydrocortisone antibody: A) with hydrocortisone but without peptide conjugation or tTG; B) with hydrocortisone but without tTG; and C) with hydrocortisone and tTG.
Figure 10B:
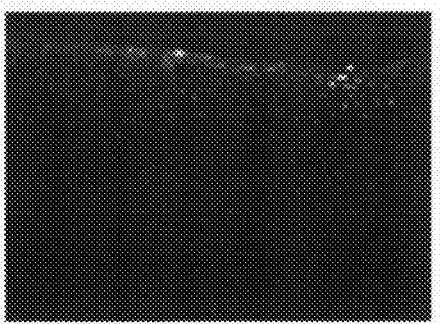
Figure 10C:
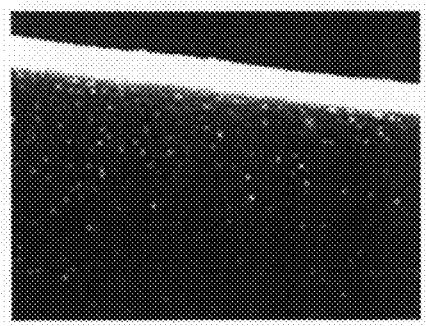

The same experiment was performed using a peptide functionalized hydrocortisone (HC-GFKG) molecule and visualized using an anti-hydrocortisone antibody. The results shown below indicate the specific coupling of this molecule to the tissue surface. (See, FIGS. 10A-C.)

Example 12a

Synthesis of Hydrocortisone Prodrugs

Hydrocortisone-GFKG prodrug (TRIP-C) was synthesized on a H-Gly-2-ClTrt resin (1 g, 0.77 mmol/g) using standard Fmoc solid phase peptide synthesis. (See FIG. 11A) Each coupling reaction was performed for 3 hours with a 10 min pre-activation of four equivalents of Fmoc-amino acid: benzotriazole-1-yl-oxy-tris(dimethylamino)-phosphonium-hexafluorophosphate (BOP):N-hydroxybenzotriazole (HOBt):diisopropylethylamine (DIEA) (1:1:1:1) in N-methylpyrrolidinone (NMP) at room temperature. The Fmoc was removed by 20% piperidine in NMP for 1 hour. After Fmoc removal from the N-terminal amino acid, hydrocortisone 21-hemisuccinate:BOP:HOBt:DIPEA (1:1:1:1) was added to the resin at 2 equivalents. At the completion of the reaction, the resin was washed with NMP and dichloromethane (DCM), two times each, and then treated with 50% trifluoroacetic acid (TFA) in DCM for 1 hour. The crude product was obtained by concentration of the TFA solution and addition of diethyl ether. Purification was performed using semi-preparative RP-HPLC using a C-18 column (250×22 mm, 10 µm, Vydac) and an acetonitrile gradient of 15-46% in water with 0.1% TFA for 120 min. The purified TRIP-C was then frozen, lyophilized and stored at −20° C. until use. The product was analyzed by ESI-MS analysis on a LCQ LC-MS system (Finnigan, Thermoquest, CA) and purity was verified using RP-HPLC on a C18 column (250×4.6 mm, 10 µm, Vydac) with an acetonitrile gradient of 20-55% in water with 0.1% TFA for 30 min with detection at 242 nm.

Example 12b

For synthesis of hydrocortisone-GFKG-PEG, TRIP-PC (FIG. 11B), the TRIP-C portion was synthesized as described above and then treated 3 times with 30% hexafluoroisopropanol (HFIP) in DCM, 10 minutes each. HyC-GFK(boc)G product was obtained by concentration of the HFIP solution and addition of 1:1 diethyl ether:hexane. The coupling of the protected peptide to the mPEG-NH$_2$ was performed overnight with a 10 min pre-activation of 1.5 equivalents of the HyC-GFK(boc)G:BOP:HOBt:DIEA (1:1:1:1) in NMP at room temperature. The product was collected by precipitation in diethyl ether and dried overnight under vacuum. Boc was removed with 50% TFA in DCM for 1 hour and the crude product was obtained by concentration of the TFA solution and addition of diethyl ether. Purification was performed using semi-preparative RP-HPLC on a C-18 column with an acetonitrile gradient of 25-55% for 120 min. TRIP-PC was then frozen and lyophilized. The product was analyzed using MALDI-TOF MS analysis on a PE Voyager DE-Pro MALDI-TOF Mass Spectrometer (Perspective Biosystems, MA) and verified on RP-HPLC with a C-18 column with an acetonitrile gradient of 24-55% and detected at 242 nm. The final product was stored at −20° C. until use.

Example 12c

Hydrolysis of the Hydrocortisone Prodrugs in Solution

The hydrolysis of 1.0 mM TRIP-C in Buffer 1 (see Table 1 for buffer compositions) was studied at 4, 23, and 37° C., in Buffer 2 at 4° C., and in Buffer 3 at 37° C. The hydrolysis of 1.0 mM TRIP-PC was evaluated in Buffer 1 at 37° C. A 30 µL portion of each sample was collected at 0.5, 1, 2, 4, 7, 24, and 48 hours and added to a 60 µL mixture of water:acetonitrile:TFA (79:20:1) to prevent further hydrolysis. This solution also contained 2 mM 6α-methyl prednisolone as an internal standard. The samples were then stored at −20° C. until analyzed with RP-HPLC and eluted with a linear gradient of 24-55% acetonitrile in water with 0.1% TFA. The amount of hydrocortisone hydrolyzed from the prodrug was determined by comparing its peak area to that of 6α-methyl prednisolone. The $T_{50}$% of the prodrug was calculated from 0.693/S, where S is the mean slope giving the best correlation coefficient in the linear part of the logarithmic curve of unhydrolyzed prodrug (1-[hydrocortisone]) versus time. The hydrolysis of 1.0 mM TRIP-C was also studied in 75% normal synovial fluid in Buffer 1 at 37° C. Thirty microliter samples were collected at 10, 20, 30, and 60 minutes and analyzed as previously described.

Example 13

Cartilage and Meniscus Isolation and Preparation

Cartilage and meniscus blocks (15 mm×17 mm×5 mm) were cut from the femoral trochea and meniscus, respectively, of 22-week old calves and stored at −80° C. until use. Before use, pieces were thawed in Buffer 1, then rinsed with Buffer 3.

Example 14

Coupling of Hydrocortisone Prodrugs to Cartilage and Meniscus Tissues

Figure 12:
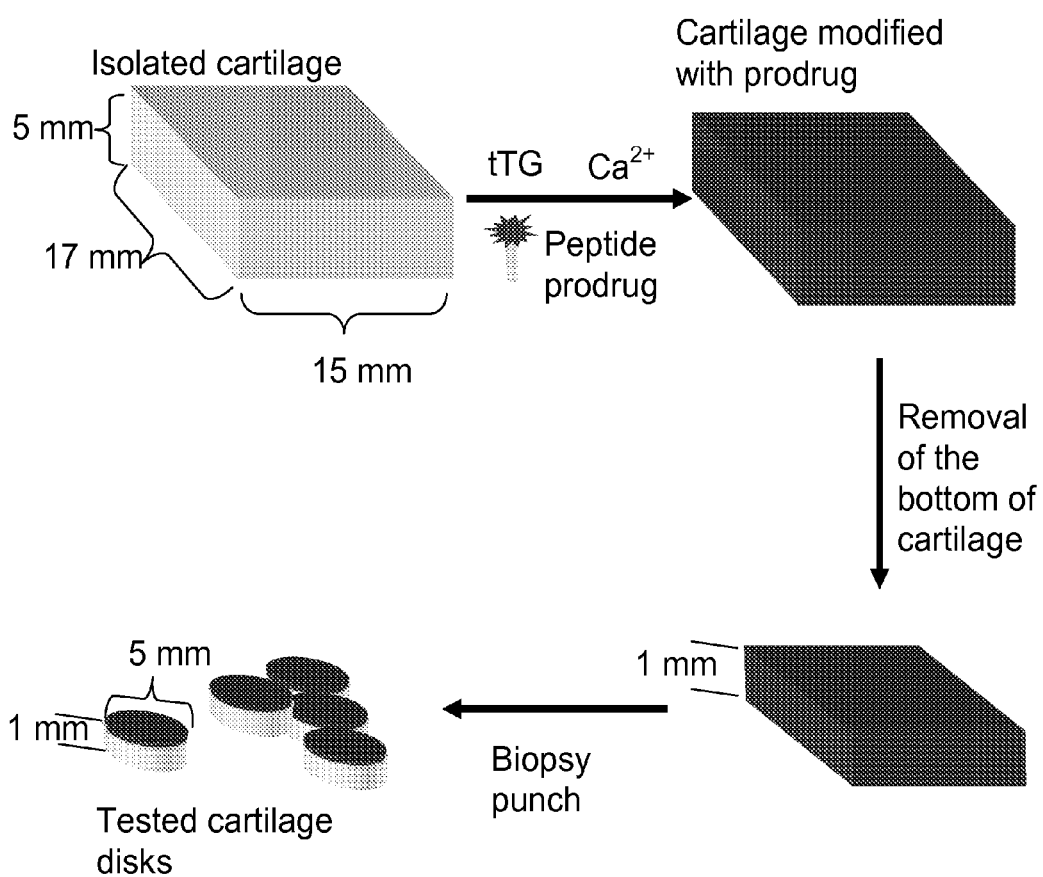
FIG. 12. Schematic of articular surface modification with prodrugs. Both TRIP-C and TRIP-PC were treated in the same manner for the tTG reaction. After the coupling reaction, 4 mm were removed from the bottom of the cartilage piece. A biopsy punch was then used to isolate disks with 5 mm diameter, having only the articular surface modified with the prodrug.

A general scheme of the covalent coupling of hydrocortisone prodrugs to cartilage is shown in FIG. 12. Cartilage or meniscus blocks were incubated in 3 mL of 1.0 mM TRIP-C, 1 U/mL tTG, and Buffer 3 for 60 min at 37° C. Control experiments were performed in the absence of tTG. At the end of the coupling reaction, the tissue blocks were rinsed 3 times in 3 mL of Buffer 1 for 5 min each at room temperature, after which the articular surface was cut. Five 5 mm disks were cut from each piece of treated tissue using a biopsy punch, with the thickness of each disk being 1 mm. The disks were rinsed overnight in 3 mL of Buffer 2 containing protease inhibitors (at the concentration recommended by the manufacturer) at 4° C., followed by rinsing for 1 hour in Buffer 1 to remove any residual protease solution at the same temperature. Each disk was blotted dry, the mass determined and then digested in 750 μL of PBS with 125 μg/mL papain, 5 mM EDTA and 5 mM cysteine at pH 6 overnight. A portion of the solution containing the digested disk was analyzed using the cortisol assay kit (used per the manufacturer's protocol) to determine the amount of hydrocortisone in the sample. The assay plate was analyzed using the Tecan (Research Triangle Park, N.C.) plate reader system. The quantity of hydrocortisone detected in each sample was normalized to the mass of the disk.

The relationship between concentration and coupling was evaluated for TRIP-C at 0.1, 0.5, 1.0, 1.5, and 2.0 mM. The effect of time on the amount of TRIP-C coupled was evaluated at 0.25, 0.5, 1.0, and 2.0 hours using 1.0 mM of the prodrug. In order to study the effect of PEG on coupling, 1.0 mM TRIP-PC was coupled to the articular surface of cartilage in the same manner as TRIP-C. These experiments were conducted and analyzed as previously described.

Example 15

Release of Hydrocortisone from the Coupled Prodrugs on the Articular Surface of Cartilage TRIP-C and TRIP-PC prodrugs were coupled to the articular surface as described above except that all solutions were filter sterilized and manipulation of the cartilage was performed in a sterile laminar flow hood. After the overnight rinse in Buffer 2 with protease inhibitors and the subsequent washes with Buffer 1, each sample was incubated in 100 μL of sterile Buffer 1, normal bovine synovial fluid, or human osteoarthritic synovial fluid at 37° C. At designated time points (4, 12, 24, 48 hours), 10 μL of the fluid were removed from each sample and replaced with 10 μL of fresh fluid. At the end of the experiment, the samples were digested and analyzed as previously described. All samples were tested in triplicate and control experiments were performed with hydrocortisone and TRIP-C in the absence of tTG and evaluated as described above.

Example 16

Immunohistochemistry

Modified tissue samples were immersed in tissue freezing media and frozen at −80° C. until use. Tissue slices (25 μm thick) were cut using a cryostat (Microm HM505N, Carl Zeiss) and the freezing media was removed with 3 washes of Buffer 1. Blocking was performed with 4% goat serum in Buffer 1 (blocking buffer) for 1 hour at room temperature. The tissue sections were then incubated with 10 μg/mL mouse anti-hydrocortisone antibody for 1.5 h in the blocking buffer at room temperature, rinsed 3 times with Buffer 1 for 5 minutes each, and then incubated with fluorescein conjugated goat anti-mouse antibody (1/200) in blocking buffer for 1 hour. Samples were rinsed again with Buffer 1 and then imaged using a Leica epifluorescent microscope ($\lambda_{ex}$=495 nm, $\lambda_{em}$=520 nm for fluorescein) and a SPOT RT digital camera (Diagnostic Instruments, Sterling Heights, Mich.).

Example 17

Statistical Analysis

Statistical analysis was performed using one-way ANOVA and Tukey's post-hoc test with 95% confidence intervals with SPSS (SPSS, Chicago, Ill.).

Example 18

Mass Spectrometry and RP-HPLC Analysis of Prodrugs

On RP-HPLC, TRIP-C had a retention time of 21.1 minutes and ESI-MS analysis of the product gave an observed mass of 852.78 Da (calculated 851.99). MALDI-TOF analysis of TRIP-PC yielded a mass distribution consistent with the presence of a polydispersed PEG. The mass distribution was centered at 5.8 kDa, demonstrating successful conjugation of the peptide (852 Da) to PEG (5 kDa). On RP-HPLC, TRIP-PC had a retention time of 24.0 min, with an additional peak at 23.0 min, accounting for a 7% impurity in the sample.

Example 19

Hydrolysis of Hydrocortisone Prodrugs in Solution

A sample chromatogram of partially hydrolyzed TRIP-C combined with 6α-methyl prednisolone. Using a 24-55% gradient of acetonitrile in water, hydrolyzed hydrocortisone, 6α-methyl prednisolone, and TRIP-C had retention times of 10.1, 14.0, and 16.5 minutes, respectively. A similar chromatogram was observed for TRIP-PC, but with a retention time of 24.0 minutes. Integration of peak area for samples hydrolyzed for different lengths of time allowed for calculation of $T_{50}$% values, which are listed in Table 2, below. As the incubation temperature decreased, the $T_{50}$% of hydrolysis of TRIP-PC increased in Buffer 1 from 50.2 min at 37° C. to 57.8 hours at 4° C. A decrease of 3 pH units, from 7.4 to 4.0 at 4° C., also led to an increase in $T_{50}$% of hydrolysis by a factor of 33. In Buffer 3 at 37° C., the $T_{50}$% (27.6 min) was lower than in Buffer 1 at the same temperature. Hydrolysis of TRIP-C was 4 times more rapid in synovial fluid than in Buffer 1 at 37° C. Finally, $T_{50}\%$ of TRIP-C and of TRIP-PC, 51.1 minutes, were comparable in Buffer 1 at 37° C.

TABLE 2

Solution hydrolysis of TRIP-C at various conditions.

| Hydrolysis Conditions | Buffer | Temperature (° C.) | $T_{50\%}$ (minutes) |
|---|---|---|---|
| PBS, pH 7.4 | Buffer 1 | 37 | 50.2 |
| PBS, pH 7.4 | Buffer 1 | 23 | 198 |
| PBS, pH 7.4 | Buffer 1 | 4 | 3465 |
| PBS, pH 4.0 | Buffer 2 | 4 | 115500 |
| Synovial Fluid | | 37 | 11.1 |
| 10 mM $CaCl_2$, 40 mM HEPES, 100 mM NaCl, pH 7.4 | Buffer 3 | 37 | 27.6 |

Example 20

Coupling of TRIP-C to the Articular Surface

Figure 13:
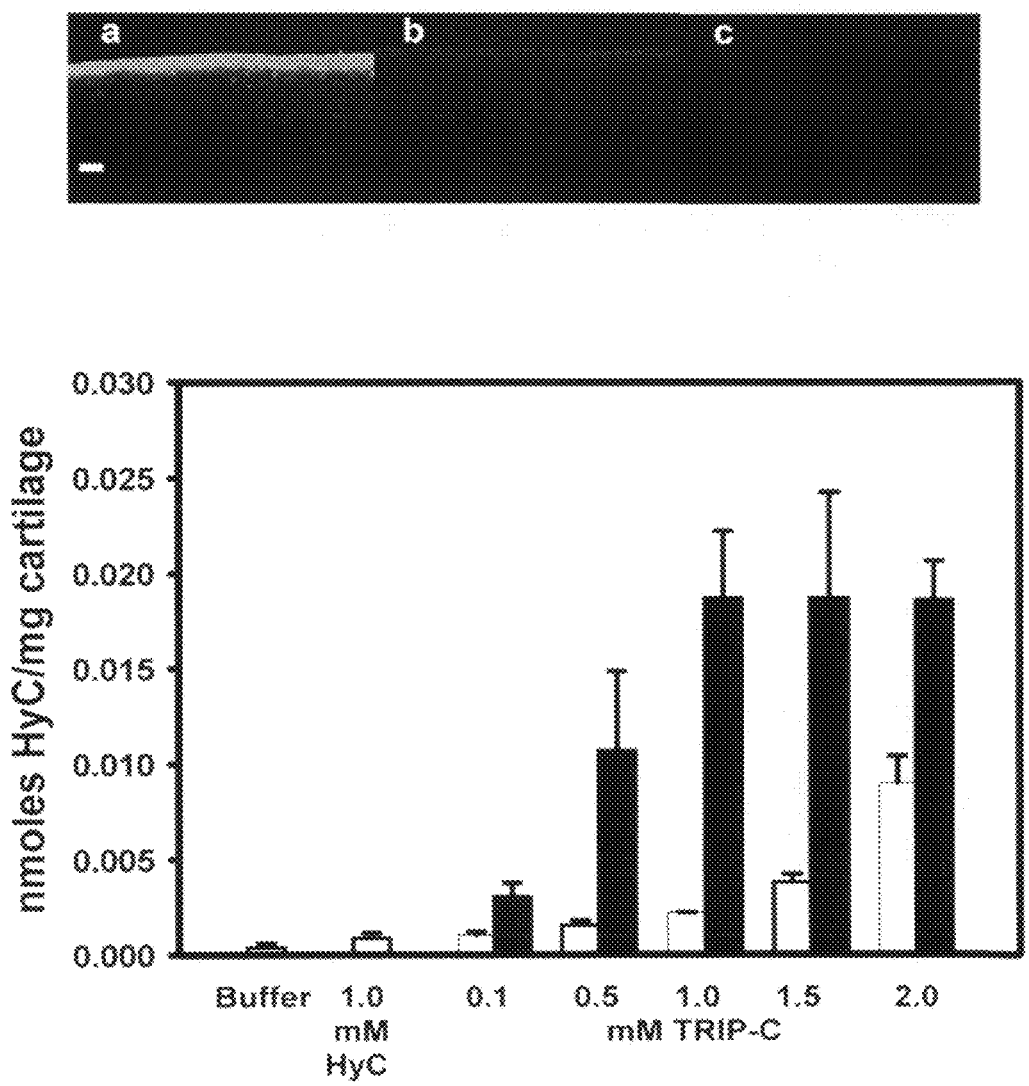
FIGS. 13A-D. Enzymatic coupling of TRIP-C on the articular surface of cartilage. A-C) Digital images showing immunodetection of bound TRIP-C using an anti-hydrocortisone antibody and fluorescein conjugated secondary antibody. Bar in (A) represents 30 μm. Cartilage was incubated in Buffer 3 with A) 1.0 mM TRIP-C with tTG; B) 1.0 mM TRIP-C; C) 1.0 mM hydrocortisone. D) Graph quantifying the amount of hydrocortisone (HyC) detected on the cartilage after incubation with 0.1 mM to 2 mM of TRIP-C. Control samples are incubated with buffer only. Error bars represent standard deviations. *, $p<0.05$ as compared to 1.0 mM with tTG. †, $p<0.05$ comparing samples treated with and without tTG.

Incubation of TRIP-C with cartilage in the presence of tTG resulted in coupling of the prodrug to the articular surface, as evidenced by the intense immunofluorescence on the tissue surface (FIG. 13A). When either TRIP-C or hydrocortisone were incubated with cartilage in the absence of tTG, no immunofluorescence was detected (FIGS. 13B-C). Quantification of the amount of hydrocortisone on the tissue surface yielded 0.0187±0.0035 nmoles/mg of tissue of coupled TRIP-C. Nonspecific adsorption of TRIP-C and hydrocortisone to the tissue resulted in a minimal amount of hydrocortisone detected on the tissue surface and when quantified, was significantly (p<0.05) lower than TRIP-C was incubated with tTG. This indicates that the majority of hydrocortisone detected in the tTG treated samples was bound to the tissue via the action of tTG.

To determine the effect of TRIP-C concentration on the amount of prodrug enzymatically coupled to the articular surface, cartilage blocks were incubated with different concentrations of TRIP-C for 1 hour. With the exception of the lowest concentration (0.1 mM) examined, the samples incubated with tTG had significantly (p<0.05) larger quantities of TRIP-C detected than the respective control samples without tTG (FIG. 13D). The amount of hydrocortisone bound to the tissue increased in a linear fashion between 0.1 mM and 1 mM but did not increase further between 1.0 and 2.0 mM.

Figure 14:
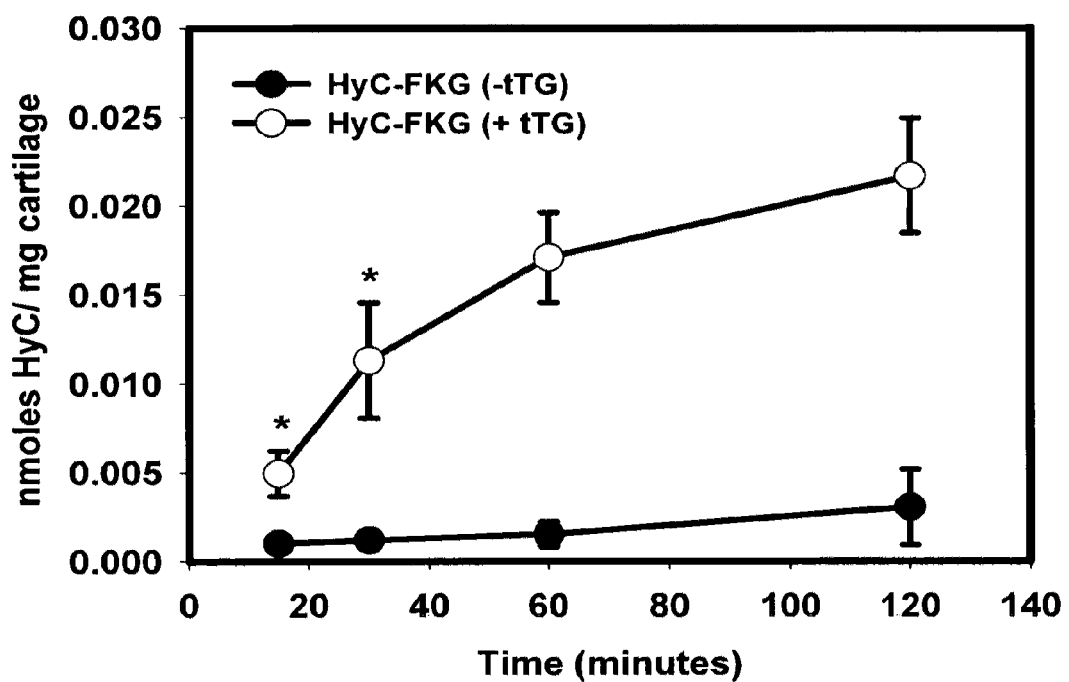
FIG. 14. Time dependence of enzymatic coupling of TRIP-C to the articular surface. The amount of hydrocortisone (HyC) detected increased as time increased for samples incubated in 1.0 mM of TRIP-C and 1 U/mL tTG. There was no statistical increase in the samples that did not contain tTG. *, p<0.05 comparing the amount of hydrocortisone detected after 15 and 30 minutes of coupling to the amount after 60 minutes of coupling.

The time dependency of TRIP-C coupling to cartilage was determined at a prodrug concentration of 1.0 mM. The results revealed a gradual increase in enzyme catalyzed prodrug coupling to the tissue over a period of 120 minutes (FIG. 14). In addition, the rate of coupling decreased as the time increased. Incubation of TRIP-C with cartilage in the absence of tTG resulted in nonspecific adsorption which did not statistically increase over the course of the experiment.

Example 21

Effect of PEG on Prodrug Coupling

Addition of a C-terminal PEG to the prodrug did not significantly impact enzymatic coupling to the tissue surface, as both immunohistochemistry and hydrocortisone quantification demonstrated no detectable difference in bound hydrocortisone between TRIP-C and TRIP-PC (FIGS. 15A, C, and E). In addition, the levels of nonspecific binding were similar for the two in the absence of tTG (p>0.05) (FIGS. 15B, D, and E), which also indicated that the presence of PEG did not significantly increase nonspecific binding to cartilage.

Example 22

Figure 16A:
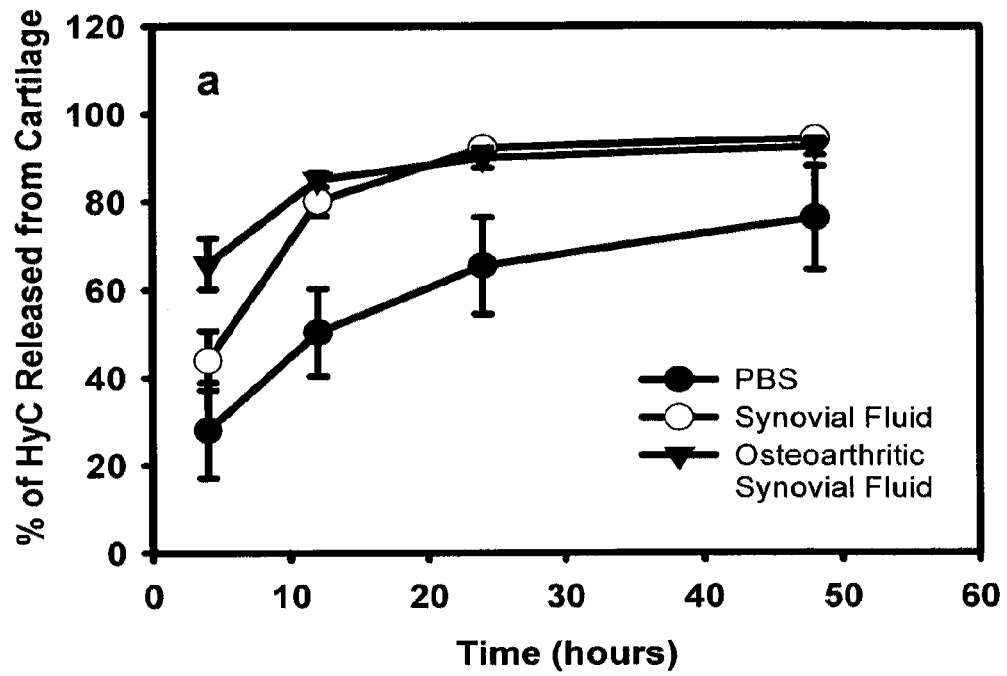
FIGS. 16A-B. Hydrolysis of hydrocortisone from coupled prodrug on the articular surface during 48 hours of incubation with Buffer 1, normal synovial fluid, and osteoarthritic fluid. Prior to the 48 hour experiment, cartilage surfaces were modified by incubating in Buffer 3 as follows: A) with 1.0 mM TRIP-C and tTG; B) with 1 mM TRIP-PC and tTG. Samples incubated with tTG had a statistical increase in the amount of hydrocortisone detected in all 3 fluids from 4 to 48 hours (p<0.05). In addition, there was significantly more hydrocortisone detected in both synovial fluids than in Buffer 1 (p<0.05).
Figure 16B:
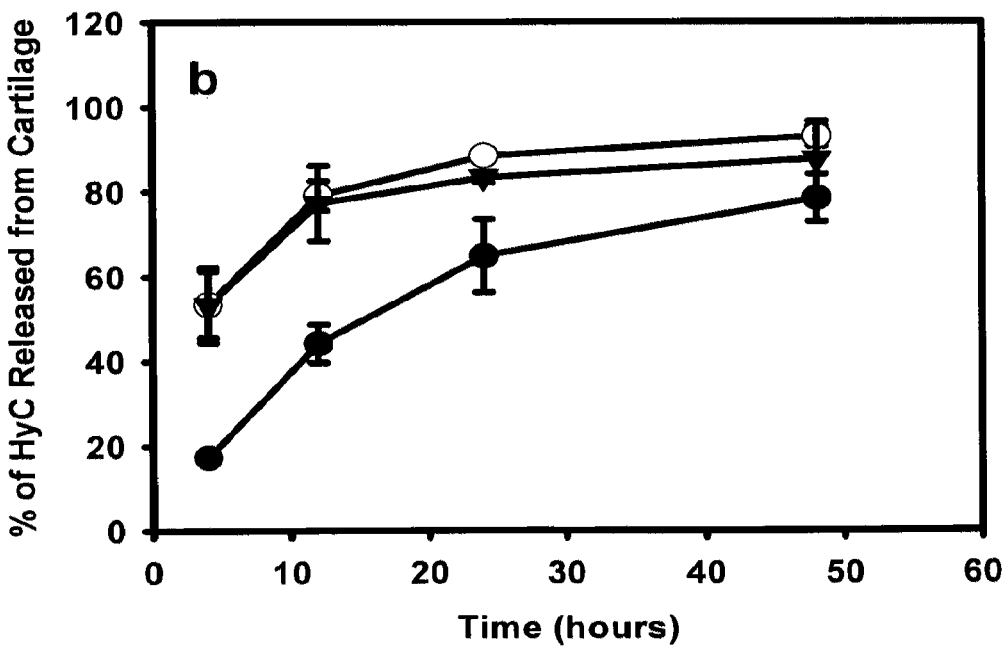

Hydrolysis of Hydrocortisone from Enzymatically Coupled Prodrug on the Articular Surface The release of hydrocortisone from tissue-bound TRIP-C and TRIP-PC were examined in buffer, bovine synovial fluid and human OA synovial fluid. From 4 to 48 hours of incubation, there was a statistical increase in the amount of hydrocortisone released from the cartilage for samples treated with tTG and TRIP-C, regardless of incubating fluid (p<0.05) (FIG. 16A). Similar results were observed with cartilage pieces modified with TRIP-PC in the presence of tTG for all fluids (p<0.05) (FIG. 16B). At 4 hours, there was statistically more hydrocortisone released in the osteoarthritic synovial fluid than in Buffer 1 for both prodrugs. When the time increased to 12 and 24 hours, there was statistically more hydrocortisone detected in both synovial fluids than in Buffer 1. However, there was no statistical difference in the amount of the hydrocortisone hydrolyzed from the prodrugs on the cartilage surface in either type of synovial fluid during the same time period. At 48 hours, all 3 solutions statistically contained the same proportion of hydrocortisone. Control experiments with hydrocortisone and TRIP-C nonspecifically adsorbed to the cartilage surface demonstrated only nonspecific release of hydrocortison.

Example 23

Immobilization of TRIP-C on Meniscus

Figure 17A:
FIGS. 17A-C. Coupling of TRIP-C to the meniscus. A and B) Digital images showing immunohistochemistry of the meniscus with anti-hydrocortisone antibody and the corresponding fluorescein conjugated secondary. A) Incubation of the meniscus with 1.0 mM TRIP-C and tTG. B) Incubation of the meniscus with 1 mM TRIP-C. Bar represents 60 µm. C) Graph comparing amount of hydrocortisone detected in cartilage with that in the meniscus. *, p<0.05, comparing the amount of hydrocortisone detected in cartilage to that in the meniscus. †, p<0.05 comparing samples treated with and without tTG.
Figure 17B:
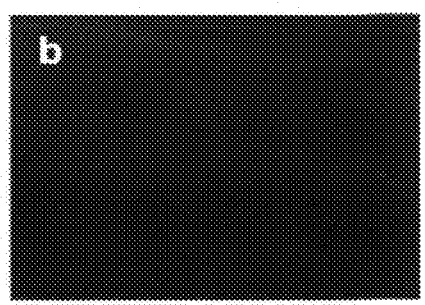
Figure 17C:
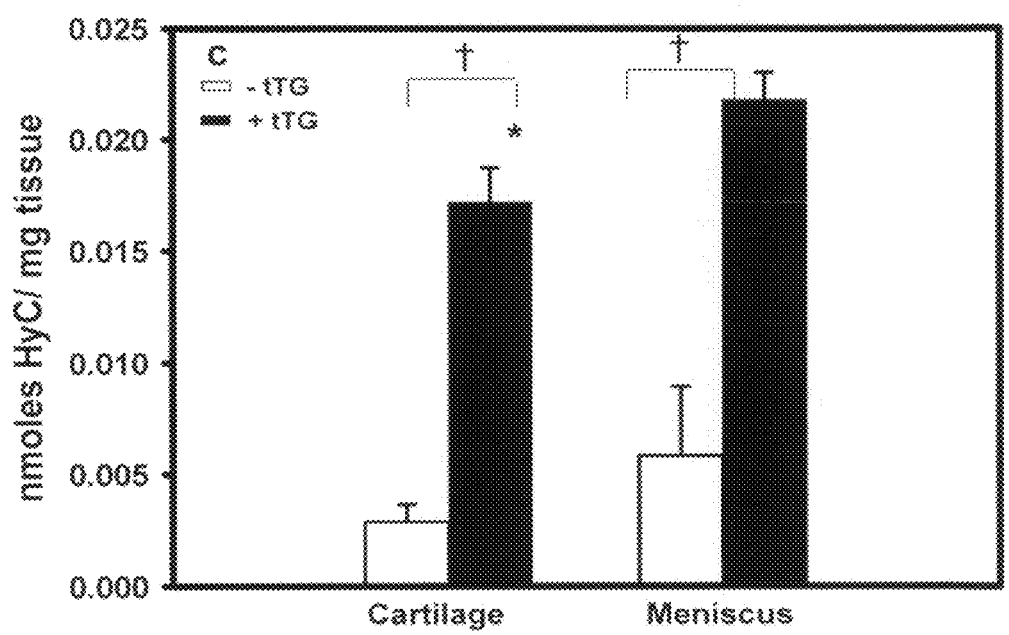

After incubation of TRIP-C and tTG with meniscus blocks, hydrocortisone was detected on the tissue surface with similar intensity as with cartilage (FIGS. 17A-B). The absence of tTG during incubation resulted in statistically (p<0.05) less hydrocortisone detected on the surface of the meniscus. A comparison of TRIP-C enzymatically incorporated into the cartilage and meniscus revealed statistically (p<0.05) greater immobilization of the prodrug on the meniscal tissue (FIG. 17C). The nonspecific binding of TRIP-C to cartilage and meniscus was statistically similar between groups.

Initial results demonstrated that synthetic peptide and peptide-polymer conjugates can be enzymatically coupled to cartilage under mild conditions through the formation of isopeptide bonds between the peptide and ECM proteins. Cartilage is only one example of a tissue with a surface readily accessible through minimally invasive administration of solutions containing tTG and synthetic molecules. Reactive cartilage ECM components can also be found in many other connective tissues, indicating broad applicability of this invention.

More specifically, the preceding data demonstrate transglutaminase immobilization of prodrug molecules onto tissue surfaces as a means of providing localized drug delivery. Hydrocortisone was chemically conjugated to a tTG substrate peptide via a hydrolysable ester linkage and used in conjunction with tTG to immobilize the prodrug onto cartilage and meniscus tissue. Tissue bound drug was then hydrolyzed under physiologic conditions to provide local release of the anti-inflammatory drug. This approach to localizing drugs at a target site is simple and can be conducted at physiologic conditions, creating a "reservoir" of hydrocortisone within the joint space from which it can elute with time. Moreover, this strategy is not limited to the intra-articular space, but can be used to immobilize therapeutic agents on or in other tissue environments.

We claim:

1. A peptide conjugate compound comprising a bioactive agent, said agent a prodrug of a glucocorticoid; a peptide component comprising at least one of a lysinyl and a glutaminyl substrate for a transglutaminase; a component coupling said agent to said peptide, said coupling component cleavable under physiological conditions; and a terminal linear monomethoxy poly(ethylene) glycol component coupled to said peptide component.

2. The compound of claim 1 wherein said peptide component comprises a sequence comprising at least one of FKG and GQQQLG (SEQ ID NO: 1).

3. The compound of claim 1 wherein said coupling moiety is hydrolysable.

4. The compound of claim 3 wherein said coupling component comprises an ester moiety.

5. The compound of claim 1 wherein said agent is a prodrug of hydrocortisone.

6. The compound of claim 1 coupled to a substrate comprising an extracellular matrix component.

7. The compound of claim 6 coupled to one of a cartilage tissue and a meniscus tissue.

8. A peptide conjugate compound comprising a prodrug of hydrocortisone; a peptide component comprising at least one of a lysinyl and a glutaminyl substrate for a transglutaminase; a component coupling said prodrug to said peptide, said coupling component cleavable under physiological conditions; and a terminal linear monomethoxy poly(ethylene) glycol component coupled to said peptide component.

9. The compound of claim 8 wherein said coupling component comprises an ester moiety.

10. The compound of claim 8 wherein said peptide component comprises a sequence comprising at least one of FKG and GQQQLG (SEQ ID NO: 1).

11. The compound of claim 8 coupled to one of a cartilage tissue and a meniscus tissue.

12. A composition comprising a compound selected from a peptide conjugate compound of claim 1 and a pharmaceutically-acceptable salt thereof; and a pharmaceutically-acceptable carrier.

13. The compound of claim 12 wherein said peptide component comprises a sequence comprising at least one of FKG and GQQQLG (SEQ ID NO: 1).

14. The composition of claim 12 wherein said coupling moiety is hydrolysable.

15. The composition of claim 12 wherein said agent is a prodrug of a glucocorticoid.

16. The composition of claim 15 wherein said agent is a prodrug of hydrocortisone.

17. The composition of claim 12 coupled to a tissue substrate comprising an extracellular matrix component.

18. A peptide conjugate compound comprising a bioactive agent selected from a glucocorticoid and a prodrug of a glucocorticoid; a peptide component comprising a lysinyl substrate for a transglutaminase, said substrate comprising a GFKG sequence; and a component coupling said agent to said peptide, said coupling component cleavable under physiological conditions.

19. The compound of claim 18 wherein said agent is a prodrug of a glucocorticoid.

20. The compound of claim 18 comprising a terminal linear monomethoxy poly(ethylene) glycol component coupled to said peptide component.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 1

Gly Gln Gln Gln Leu Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Pro Gln Gln Gln Tyr Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 3

Gly Asn Asn Asn Leu Gly
1               5
```